United States Patent
Shamain et al.

(10) Patent No.: US 11,793,425 B1
(45) Date of Patent: Oct. 24, 2023

(54) PHASE DISAMBIGUATION FOR RADAR-BASED BREATHING MEASUREMENTS

(71) Applicant: Amazon Technologies, Inc., Seattle, WA (US)

(72) Inventors: Durgaprasad Kashinath Shamain, Los Gatos, CA (US); Koohyun Um, Sunnyvale, CA (US); Morris Yuanhsiang Hsu, Santa Clara, CA (US)

(73) Assignee: Amazon Technologies, Inc., Seattle, WA (US)

( * ) Notice: Subject to any disclaimer, the term of this patent is extended or adjusted under 35 U.S.C. 154(b) by 333 days.

(21) Appl. No.: 17/114,399

(22) Filed: Dec. 7, 2020

Related U.S. Application Data

(60) Provisional application No. 62/985,495, filed on Mar. 5, 2020.

(51) Int. Cl.
*A61B 5/11* (2006.01)
*G16H 50/30* (2018.01)
(Continued)

(52) U.S. Cl.
CPC .............. *A61B 5/1126* (2013.01); *A61B 5/05* (2013.01); *A61B 5/113* (2013.01); *A61B 5/4815* (2013.01);
(Continued)

(58) Field of Classification Search
CPC .... G16H 50/30; A61B 5/0507; A61B 5/0816; A61B 5/4806; A61B 5/4815;
(Continued)

(56) References Cited

U.S. PATENT DOCUMENTS

| | | | |
|---|---|---|---|
| 2010/0152600 A1* | 6/2010 | Droitcour | A61B 5/1113 600/534 |
| 2011/0112425 A1* | 5/2011 | Muhlsteff | G01S 13/88 600/534 |

(Continued)

OTHER PUBLICATIONS

Subcarrier-index modulation OFDM, 2009 IEEE 20th International Symposium on Personal, Indoor and Mobile Radio Communications, 2009, pp. 177-181, doi: 10.1109/PIMRC.2009.5449882 (Year: 2009).*

(Continued)

*Primary Examiner* — Eric F Winakur
*Assistant Examiner* — Elina Sohyun Ahn
(74) *Attorney, Agent, or Firm* — Eversheds Sutherland (US) LLP

(57) ABSTRACT

Devices, systems, and methods are provided for disambiguating phase in radar-based waveforms. A method may include determining a first waveform, the first waveform associated with a first subcarrier and a second subcarrier in a frequency domain, and the first waveform based on radar measurements. The method may include determining a motion signal, and determining, based on the first subcarrier, the second subcarrier, a subcarrier spacing of the subcarriers, and the motion signal, a phase change differential value between the first subcarrier and the second subcarrier. The method may include generating, based on the phase change differential value, a second waveform, and generating a third waveform in the time domain by applying the second waveform to the first waveform.

20 Claims, 11 Drawing Sheets

(51) Int. Cl.
*G16H 40/67* (2018.01)
*A61B 5/05* (2021.01)
*G01S 7/41* (2006.01)
*A61B 5/00* (2006.01)
*G01S 13/88* (2006.01)
*A61B 5/113* (2006.01)

(52) U.S. Cl.
CPC .............. *A61B 5/7275* (2013.01); *G01S 7/41* (2013.01); *G01S 13/88* (2013.01); *G16H 40/67* (2018.01); *G16H 50/30* (2018.01)

(58) Field of Classification Search
CPC ... A61B 5/7207; A61B 5/7239; A61B 5/7203; A61B 5/7221; A61B 5/7228; A61B 5/7278; G01S 13/282; G01S 7/415; G01S 7/2813; G01S 13/88; G01S 13/583
See application file for complete search history.

(56) References Cited

U.S. PATENT DOCUMENTS

2018/0180728 A1* 6/2018 Shamain .............. A61B 5/7253
2021/0275056 A1* 9/2021 McMahon ........... A61B 5/6898

OTHER PUBLICATIONS

Kushida, T., Tanaka, K., Aoto, T. et al. Phase disambiguation using spatio-temporally modulated illumination in depth sensing. IPSJ T Comput Vis Appl 12, 1 (2020). https://doi.org/10.1186/s41074-020-00063-x (Year: 2020).*

Gu C, Li C. Assessment of human respiration patterns via noncontact sensing using Doppler multi-radar system. Sensors (Basel). Mar. 16, 2015;15(3):6383-98. doi: 10.3390/s150306383. PMID: 25785310; PMCID: PMC4435179 (Year: 2015).*

* cited by examiner

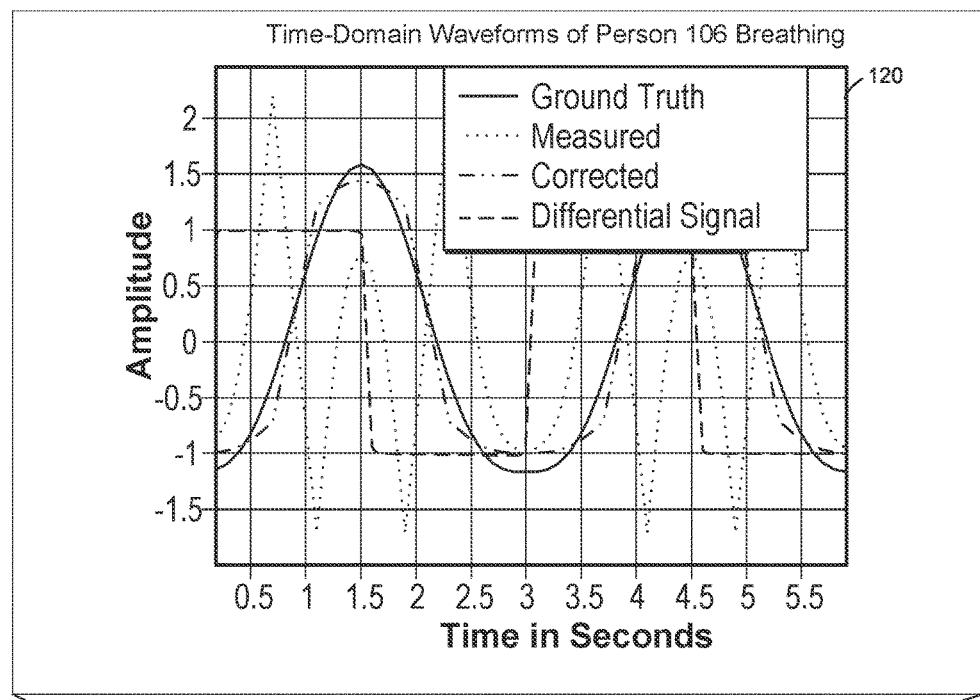
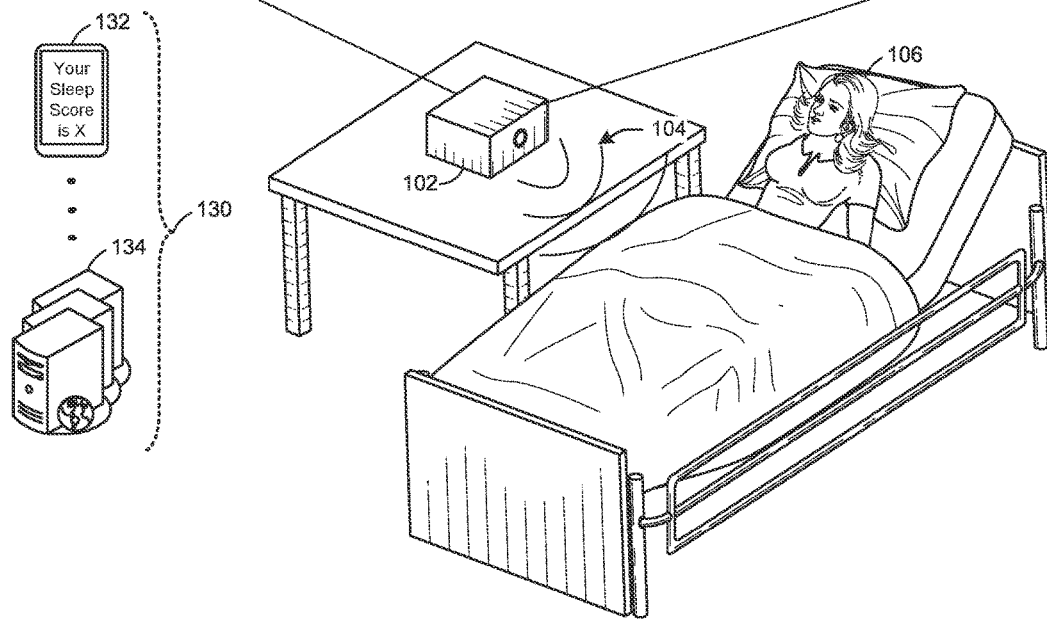
FIG. 1

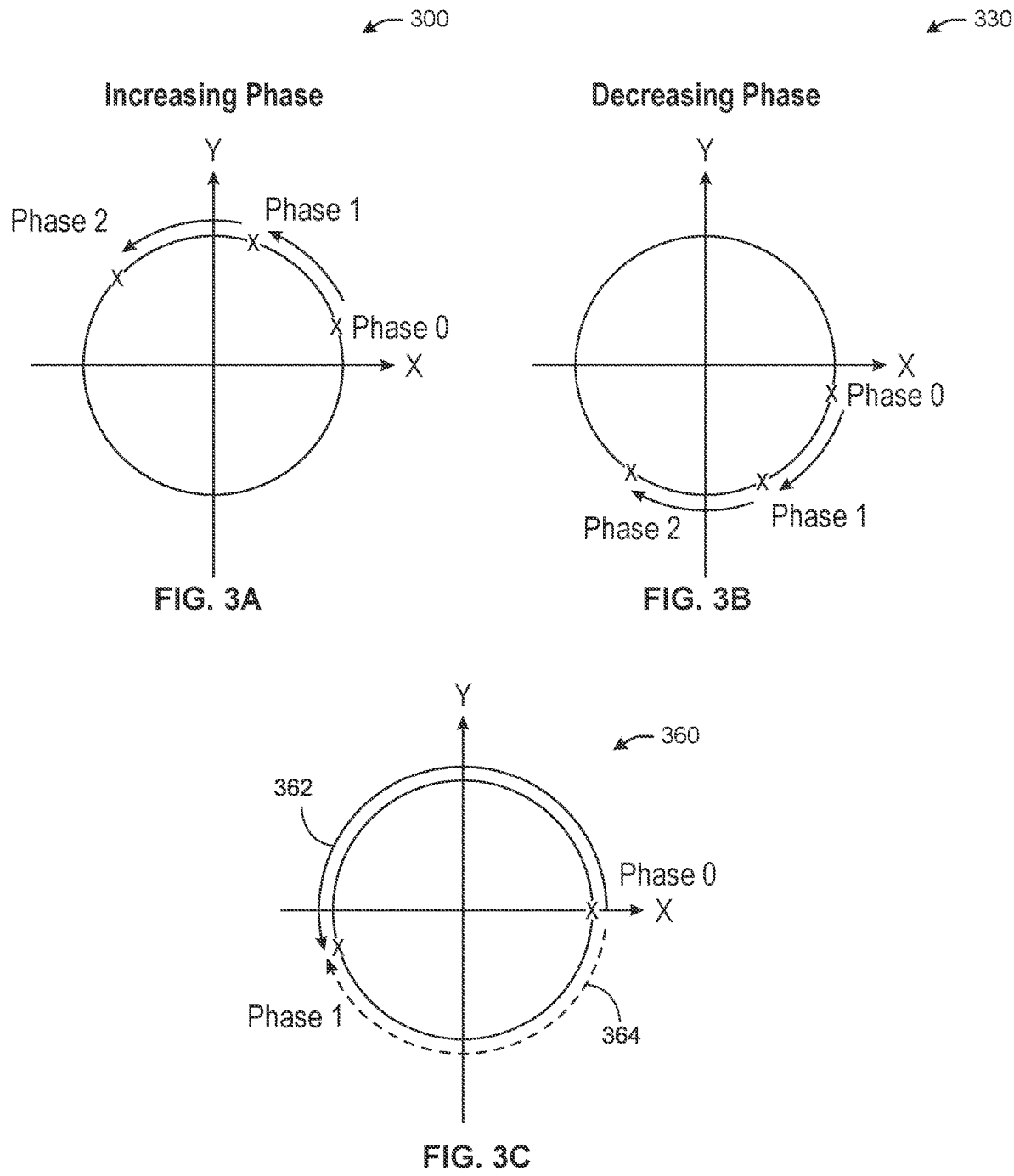
FIG. 3A, FIG. 3B, and FIG. 3C

PHASE DISAMBIGUATION FOR RADAR-BASED BREATHING MEASUREMENTS

CROSS-REFERENCE TO RELATED APPLICATION(S)

This application is related to and claims priority to U.S. Provisional Patent Application No. 62/985,495, filed Mar. 5, 2020, which is hereby incorporated herein by reference in its entirety.

BACKGROUND

People increasingly are relying on devices to analyze their health. Devices may examine wireless signals to analyze a person's health. For example, devices may analyze signals indicative of motion. However, some waveforms may exhibit phase ambiguity that may cause analyses of the waveforms to be inaccurate. There is therefore a need for phase disambiguation for radar-based measurements.

BRIEF DESCRIPTION OF THE DRAWINGS

FIG. 1 illustrates an example system for phase disambiguation for radar-based breathing measurements, in accordance with one or more example embodiments of the present disclosure.

FIG. 3A illustrates an example phase increase of a signal used for radar-based breathing measurements, in accordance with one or more example embodiments of the present disclosure.

FIG. 3B illustrates an example phase decrease of a signal used for radar-based breathing measurements, in accordance with one or more example embodiments of the present disclosure.

FIG. 3C illustrates an example of phase ambiguity of a signal used for radar-based breathing measurements, in accordance with one or more example embodiments of the present disclosure.

Figure 2:
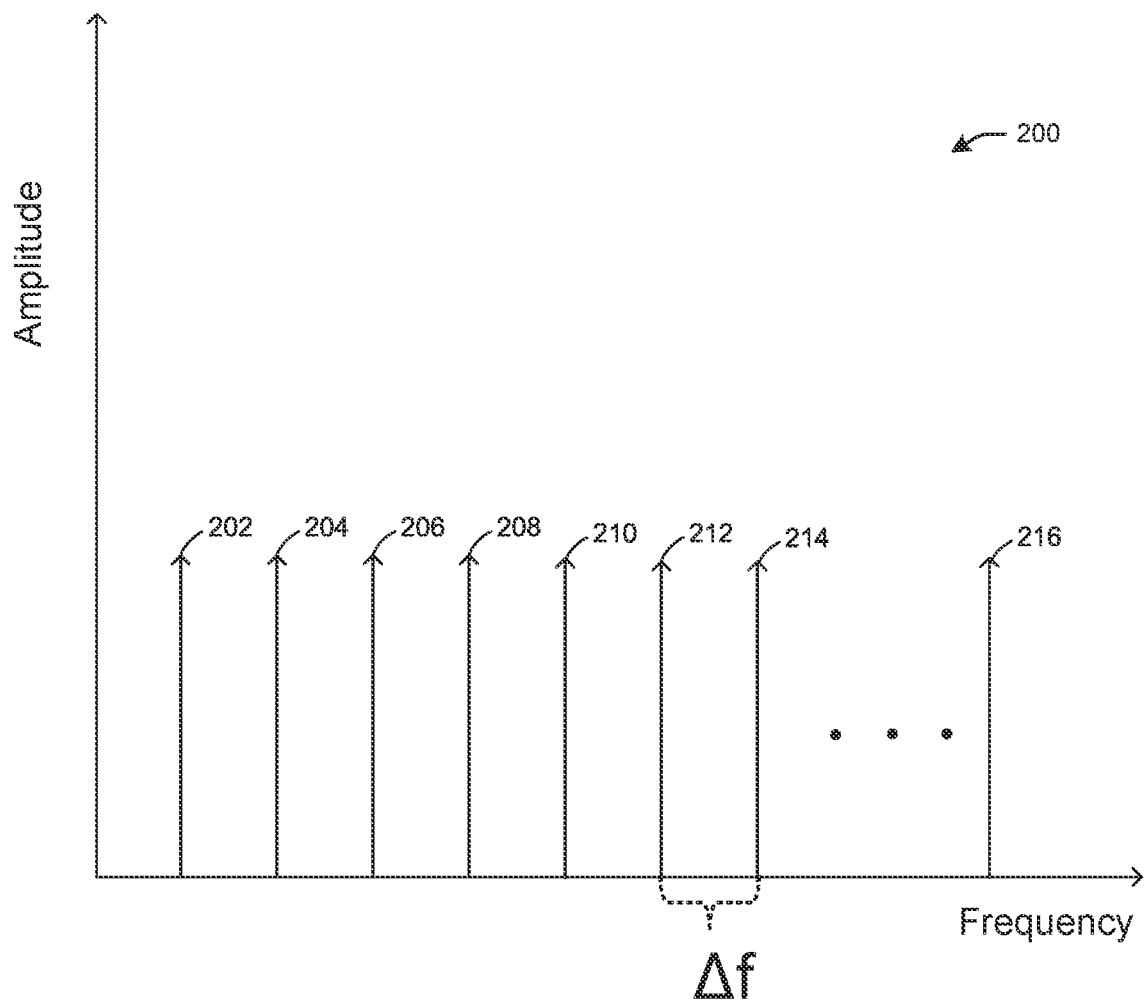
FIG. 2 illustrates example subcarriers of a signal, in accordance with one or more example embodiments of the present disclosure.

Certain implementations will now be described more fully below with reference to the accompanying drawings, in which various implementations and/or aspects are shown. However, various aspects may be implemented in many different forms and should not be construed as limited to the implementations set forth herein; rather, these implementations are provided so that this disclosure will be thorough and complete, and will fully convey the scope of the disclosure to those skilled in the art. Like numbers in the figures refer to like elements throughout. Hence, if a feature is used across several drawings, the number used to identify the feature in the drawing where the feature first appeared will be used in later drawings.

DETAILED DESCRIPTION

Overview

Example embodiments described herein provide certain systems, methods, and devices for phase disambiguation for radar-based breathing measurements.

Devices may measure a variety of motion and vibrations such as a person's breathing to determine whether the person's breathing is indicative of health issues and to determine a person's sleep efficiency. The propagation of radar waves that encounter a person or object may reflect due to the presence of the person (e.g., a person inhaling and exhaling) or object, and the detection of the reflected radar waves may result in a waveform that represents the person's breathing (or object motion/vibration), and which may be analyzed to determine a person's health and sleep efficiency (or the motion/vibration of an object).

Radar allows for the measurement of a breathing person's chest movement (or other motion/vibration) by measuring the radiofrequency (RF) phase of a waveform. Radar waveforms, such as stepped frequency continuous-waveforms (SFCWs), include multiple subcarriers. Orthogonal Frequency-Division Multiplexing (OFDM) represents a multi-carrier modulation scheme that allows for modulation of multiple subcarrier signals on multiple streams or channels. A subcarrier (also referred to as tone) may refer to signal sounds in a frequency domain. Respective subcarriers of a signal may be spaced by a constant step value, and therefore may have indices referring to their location on a frequency spectrum.

Outwards and inwards chest motions (e.g., of a person breathing) may be represented as decreasing and increasing subcarrier phases, respectively. For example, an outwards chest motion may result in a counter-clockwise phase excursion, and an inwards chest motion may result in a clockwise phase excursion.

When a person's chest motion has a similar amplitude as that of an RF carrier wavelength (e.g., 5 millimeters for a 60 GHz carrier frequency), and when the sampling rate is low (e.g., infrequent), phase excursion per RF waveform subcarrier may exceed a half cycle (e.g., 180 degrees). For example, when the carrier frequency is 60 GHz, the subcarrier (e.g., tone) spacing (e.g., step value) is 100 MHz, and a person's chest motion is 3 millimeters outwards, the phase per subcarrier changes by −1.2 cycles (−432 degrees). In this manner, phase ambiguity for SFCWs and OFDM waveforms results because it is unclear in which direction the phase excursion occurred (e.g., in the clockwise or counter-clockwise direction).

A result of the phase ambiguity may be that a measured RF waveform estimating a person's breathing may not closely resemble the person's actual breathing waveform, undermining calculations that rely on the waveform data (e.g., sleep efficiency, health, etc.).

There is therefore a need for phase disambiguation for radar-based breathing measurements.

In one or more embodiments, phase ambiguity may be eliminated by relying on a differential phase change (e.g., a phase change differential value) between respective subcarriers of an RF waveform. A differential phase change refers to a difference of phase change between two subcarriers, where each subcarrier has a phase change. The phase change can be seen as on offset from a starting point (e.g., on a coordinate system). So, two subcarriers may have different offsets. Therefore, the differential phase change takes into account the difference between the phase changes of the two subcarriers. When the phase differential between two subcarriers is used to capture the direction of motion (e.g., outwards vs. inwards), any phase ambiguity is eliminated since the differential phase excursion magnitude is a small fraction of a cycle of the RF waveform. At the same time, the direction of motion may be estimated based on the differential phase. In the example described above, the phase per subcarrier changes by −1.2 cycles, or −432 degrees. However, the phase differential only changes by −0.002 cycles, or −0.72 degrees for a 3 millimeters outward breathing motion. Using the same parameters of the above example, in the event of a 3 millimeter inward motion, the phase per subcarrier in the RF wave may change by 1.2 cycles, or 432 degrees, while the differential phase may only change by 0.002 cycles, or 0.72 degrees, thereby eliminating phase ambiguity.

In particular, for a subcarrier with index "j," the subcarrier may be represented as:

$$s_j(t) = Ae^{i\left\{\left(\frac{4\pi}{\lambda} + \frac{4\pi}{c} \cdot j\Delta f\right)d(t) + p_n(t)\right\}} + n(t), \quad (1)$$

where $s_j(t)$ represents the subcarrier "j" over time "t," A is the amplitude, i is the imaginary number, $\lambda$ is the RF wavelength, c is the speed of light (e.g., $3\times10^8$ m/s), $\Delta f$ is the subcarrier spacing (e.g., step value), d(t) is the motion signal (e.g., the measured motion of a breathing person's chest or other motion of a person or object), $p_n(t)$ is the phase noise, and n(t) is the thermal noise. Similarly, the subcarrier with index "k" may be represented as:

$$s_k(t) = Ae^{i\left\{\left(\frac{4\pi}{\lambda} + \frac{4\pi}{c} \cdot k\Delta f\right)d(t) + p_n(t)\right\}} + n(t). \quad (2)$$

The phase change for the $j^{th}$ subcarrier may be represented as:

$$\left(\frac{4\pi}{\lambda} + \frac{4\pi}{c} \cdot j\Delta f\right) d(t) + p_n(t), \quad (3)$$

which is about $2\pi$ when d(t) is about $$\frac{\lambda}{2}.$$

In contrast, the differential phase change between the $j^{th}$ and $k^{th}$ subcarriers may be:

$$\frac{4\pi}{c}(j-k)\Delta f \ d(t), \quad (4)$$

or significantly less than $2\pi$ when d(t) is on the order of $$\frac{\lambda}{2}$$

because $$\frac{(j-k)\Delta f}{c} \cdot \frac{\lambda}{2} \ll \frac{1}{2}.$$

In this manner, the differential phase change is smaller than the phase change, and has the benefit of being immune to phase noise because the phase noise $p_n(t)$ is absent from the differential phase equation.

In one or more embodiments, a device may estimate the differential phase and enhance its robustness when impairments such as thermal noise and phase noise are present. One method of estimating the differential phase is to determine the phase differential of adjacent subcarriers in the RF waveform, and then average the phase differential across all the subcarriers of the RF waveform (e.g., frequency domain averaging). Another method of estimating the differential phase is to determine the phase differential of each subcarrier with the end (e.g., edge) subcarriers of the RF waveform, and to determine weighted averages (e.g., based on the frequency difference) across all the subcarriers of the RF waveform (e.g., frequency domain weighted averaging). Another method of estimating the differential phase is to correct an erroneous isolated differential phase measurement of the RF waveform (e.g., time domain state machine). Differential phase may be a binary signal (e.g., plus or minus) and has the same periodicity as the RF breathing waveform. The differential phase may indicate the direction of breathing motion (e.g., inwards or outwards). When an isolated differential phase measurement is erroneous (e.g., flips in sign from plus to minus), the device may correct the measurement using the preceding and subsequent measurements having the correct sign. A finite state machine may be used to correct the isolated errors.

In one or more embodiments, a device may use a correcting signal (e.g., a phase correcting signal) to correct a measured RF waveform indicative of breathing. The correcting signal may indicate the direction of a true phase trend (e.g., whether the phase trend is positive or negative from one subcarrier to another). The observed phase excursion of a measured RF signal may experience abrupt changes in direction as a result of a phase excursion being more than a half cycle of the corresponding RF waveform. The correction signal may be determined using one of the above-described methods for estimating the differential phase. By applying the correction signal to the measured RF waveform that is generated based on phase ambiguity, the device may generate a corrected RF waveform that is more representative of a ground truth breathing waveform, and therefore may allow the device or another device to analyze the corrected RF waveform for health and/or sleep determinations.

In one or more embodiments, the correcting signal may indicate the direction of true phase trend (e.g., whether the phase difference between subcarriers associated with a measured RF signal is positive or negative in value). In this manner, when the correcting signal is positive, (e.g., greater than zero), the true phase trend of the measured RF signal is increasing, and when the correcting signal is negative (e.g., less than zero), the true phase trend of the measured RF signal is decreasing. The observed phase excursion for the measured RF signal may experience abrupt changes in value as a result of more than half cycle excursion (e.g., a cycle of the corresponding RF waveform). In one embodiment, the correcting signal may be based on the sign (e.g., positive or negative) of the phase difference between successive samples of the differential phase between subcarriers (e.g., whether Equation 4 results in a positive or negative value for two respective subcarriers). The following describes phase correction based on two successive samples of the measured signal and the value of the correcting signal at a given instant.

When the correcting signal indicates an increasing phase trend (e.g., a positive value), but the waveform based on the measured RF signal indicates a decreasing phase trend, the correction of the measured RF signal may include a use of phase wrapping (e.g., adding a forward $2\pi$ phase jump to the measured RF signal) to generate the corrected signal: Corrected signal(i)=Corrected signal (i−1)+$2\pi$+(measured RF signal(i)−measured RF signal(i−1)). When the correcting signal indicates a decreasing phase trend (e.g., a negative phase change between subcarriers), but the waveform based on the measured RF signal indicates an increasing phase trend, the correction of the measured RF signal may include phase wrapping (e.g., adding a backward $2\pi$ phase jump to the measured RF signal) to generate the corrected signal: Corrected signal(i)=Corrected signal(i−1)−$2\pi$+(measured RF signal(i)−measured RF signal(i−1)). When both the correcting signal and the waveform based on the measured RF signal indicate a positive or negative phase trend (e.g., both indicate a positive phase trend or both indicate a negative phase trend), no correction of the measured RF signal may be required: Corrected signal(i)=Corrected signal(i−1)+(measured RF signal(i)−measured RF signal(i−1)). The application of the correcting signal is explained further with regard to FIG. 4C. In this manner, the corrected signal may be generated by comparing the phase trend of the correcting signal to the phase trend of the measured RF signal. In one or more embodiments, the phase disambiguation described herein may apply to waveforms based on motion caused by actions and/or operations other than breathing, such as mechanical vibrations, bodily vibrations not caused by breathing, and the like.

The above descriptions are for purposes of illustration and are not meant to be limiting. Numerous other examples, configurations, processes, etc., may exist, some of which are described in greater detail below. Example embodiments will now be described with reference to the accompanying figures.

Illustrative Processes and Use Cases

FIG. 1 illustrates an example system 100 for phase disambiguation for radar-based breathing measurements, in accordance with one or more example embodiments of the present disclosure.

Referring to FIG. 1, the system 100 may include a device 102 capable of emitting and detecting radar signals 104, which may allow the device 102 to detect nearby objects, such as a person 106, whose breathing may result in RF waves 120. In particular, the device 102 may have access to a ground truth wave (e.g., indicative of the person's actual chest movements while breathing), a measured wave (e.g., the actual measured RF signal based on the radar signals 104), a differential signal wave used to disambiguate the measured wave, and a corrected wave (e.g., the differential signal wave applied to the measured wave). In this manner, while the measured wave (e.g., the wave based on the measured RF signal) differs significantly from the ground truth wave because of phase ambiguity of the measured wave, the device 102 may apply the differential signal to the measured signal to correct the phase ambiguity and generate the corrected wave, which should be more similar to the ground truth wave than to the measured wave.

Still referring to FIG. 1, the device 102 may be in communication with one or more additional devices 130 (e.g., device 132, device 134). Any of the device 102 and/or the one or more additional devices 130 may determine any of the RF waves 120. For example, the device 102 may detect the measured wave and may use the differential signal to generate the corrected wave, or the device 102 may send the measured wave to the one or more additional devices 130 to generate the corrected wave. Any of the device 102 and/or the one or more additional devices 130 may use the corrected wave to determine a sleep efficiency score of the person 106 (e.g., by determining when the corrected wave indicates that a person is asleep and/or awake). For example, the sleep score may represent a ratio of the amount of time that the person 106 is in bed to the amount of time that the person 106 is asleep. Any of the device 102 and/or the one or more additional devices 130 may use the corrected wave to determine a sleep stage (e.g., wake, light, deep, REM) by matching the corrected wave to known waves associated with a sleep stage. Any of the device 102 and/or the one or more additional devices 130 may use the corrected wave to determine when the person 106 is not breathing. Any of the device 102 and/or the one or more additional devices 130 may use the corrected wave to generate messages (e.g., indicating sleep stages, sleep scores, recommended bed and/or wake times, etc.), and/or to perform actions such as setting alarms and/or activating or deactivating devices.

In one or more embodiments, for a subcarrier (e.g., of the measured waveform) with index "j," the subcarrier may be represented as Equation (1) defined above. Similarly, the subcarrier with index "k" may be represented as Equation (2) defined above.

In one or more embodiments, the phase change for the $j^{th}$ subcarrier may be represented as Equation (3) defined above. In contrast, the differential phase change between the $j^{th}$ and $k^{th}$ subcarriers may be represented by Equation (4) defined above. In this manner, the differential phase change is smaller than the phase change, and has the benefit of being immune to phase noise because the phase noise $p_n(t)$ is absent from the differential phase equation.

In one or more embodiments, the device 102 and/or the one or more additional devices 130 may estimate the differential phase and enhance its robustness when impairments such as thermal noise and phase noise are present. One method of estimating the differential phase is to determine the phase differential of adjacent subcarriers in the RF waveform, and then average the phase differential across all the subcarriers of the RF waveform (e.g., frequency domain averaging). Another method of estimating the differential phase is to determine the phase differential of each subcarrier with the end (e.g., edge) subcarriers of the RF waveform, and to determine weighted averages (e.g., based on the frequency difference) across all the subcarriers of the RF waveform (e.g., frequency domain weighted averaging). Another method of estimating the differential phase is to correct an erroneous isolated differential phase measurement of the RF waveform (e.g., time domain state machine). Differential phase may be a binary signal (e.g., plus or minus) and has the same periodicity as the RF breathing waveform. The differential phase may indicate the direction of breathing motion (e.g., inwards or outwards). When an isolated differential phase measurement is erroneous (e.g., flips in sign from plus to minus), the device 102 and/or the one or more additional devices 130 may correct the measurement using the preceding and subsequent measurements having the correct sign. A finite state machine of the device 102 and/or the one or more additional devices 130 may be used to correct the isolated errors.

The device 102 and/or one or more additional devices 130 may include any suitable processor-driven device including, but not limited to, a mobile device or a non-mobile, e.g., a static, device. For example, the device 102 and/or the one or more additional devices 130 may include a user equipment (UE), a station (STA), an access point (AP), a personal computer (PC), a wearable wireless device (e.g., bracelet, watch, glasses, ring, etc.), a desktop computer, a mobile computer, a laptop computer, an Ultrabook™ computer, a notebook computer, a tablet computer, a server computer, a handheld computer, a handheld device, an internet of things (IoT) device, a sensor device, a PDA device, a handheld PDA device, an on-board device, an off-board device, a hybrid device (e.g., combining cellular phone functionalities with PDA device functionalities), a consumer device, a vehicular device, a non-vehicular device, a mobile or portable device, a non-mobile or non-portable device, a mobile phone, a cellular telephone, a PCS device, a PDA device which incorporates a wireless communication device, a mobile or portable GPS device, a DVB device, a relatively small computing device, a non-desktop computer, a "carry small live large" (CSLL) device, an ultra mobile device (UMD), an ultra mobile PC (UMPC), a mobile internet device (MID), an "origami" device or computing device, a device that supports dynamically composable computing (DCC), a context-aware device, a video device, an audio device, or the like. It is understood that the above is an example, but not exhaustive, list of devices that may implement the functions described herein.

FIG. 2 illustrates example subcarriers 200 of a signal, in accordance with one or more example embodiments of the present disclosure.

Referring to FIG. 2, the measured signal of FIG. 1 may include the subcarriers 200 (e.g., subcarriers 202-216, where subcarriers 202 and 216 may be guard or edge subcarriers). Respective subcarriers may be spaced by a constant step value (e.g., Δf), and therefore may have indexes referring to their location on a frequency spectrum. Radar waveforms, such as stepped frequency continuous-waveform, may include the subcarriers 200. The phase per subcarrier may undergo more than half a cycle excursion in response to motion, thus resulting in phase ambiguity as shown and explained further with regard to FIGS. 3A-3C.

A differential phase change refers to a difference of phase change between two subcarriers, where each of the subcarriers 200 has a phase change. The phase change can be seen as on offset from a starting point (e.g., on a coordinate system). So, any two of the subcarriers 200 may have different offsets. Therefore, the differential phase change takes into account the difference between the phase changes of any two of the subcarriers 200. The phase change between subcarriers is shown in FIGS. 3A-3C.

FIG. 3A illustrates an example phase increase 300 of a signal used for radar-based breathing measurements, in accordance with one or more example embodiments of the present disclosure.

FIG. 3B illustrates an example phase decrease 330 of a signal used for radar-based breathing measurements, in accordance with one or more example embodiments of the present disclosure.

FIG. 3C illustrates an example of phase ambiguity 360 of a signal used for radar-based breathing measurements, in accordance with one or more example embodiments of the present disclosure.

Referring to FIGS. 3A-3C, the phase may be based on the measured wave of FIG. 1. In FIG. 3A, the RF phase increases counter-clockwise from phase 0, to phase 1, to phase 2. In FIG. 3B, the RF phase increases clockwise from phase 0, to phase 1, to phase 2. When a sampling rate of the device 102 of FIG. 1 is low enough, phase excursion may exceed a half cycle (e.g., may be greater than 180 degrees) of the waveform corresponding to a measured RF signal. As shown in FIG. 3C, an increasing phase 362 of more than a half cycle in the counter-clockwise direction may appear like a decreasing phase 364 in the clockwise direction, resulting in phase ambiguity. In particular, because of the low sampling rate, it may not be possible for the device 102 of FIG. 1 to determine whether phase excursion occurred in the clockwise or counter-clockwise direction, resulting in phase ambiguity. In this manner, the measured wave of FIG. 1 may be significantly different than the ground truth wave of FIG. 1. An example of this is shown in FIG. 4A.

Figure 4A:
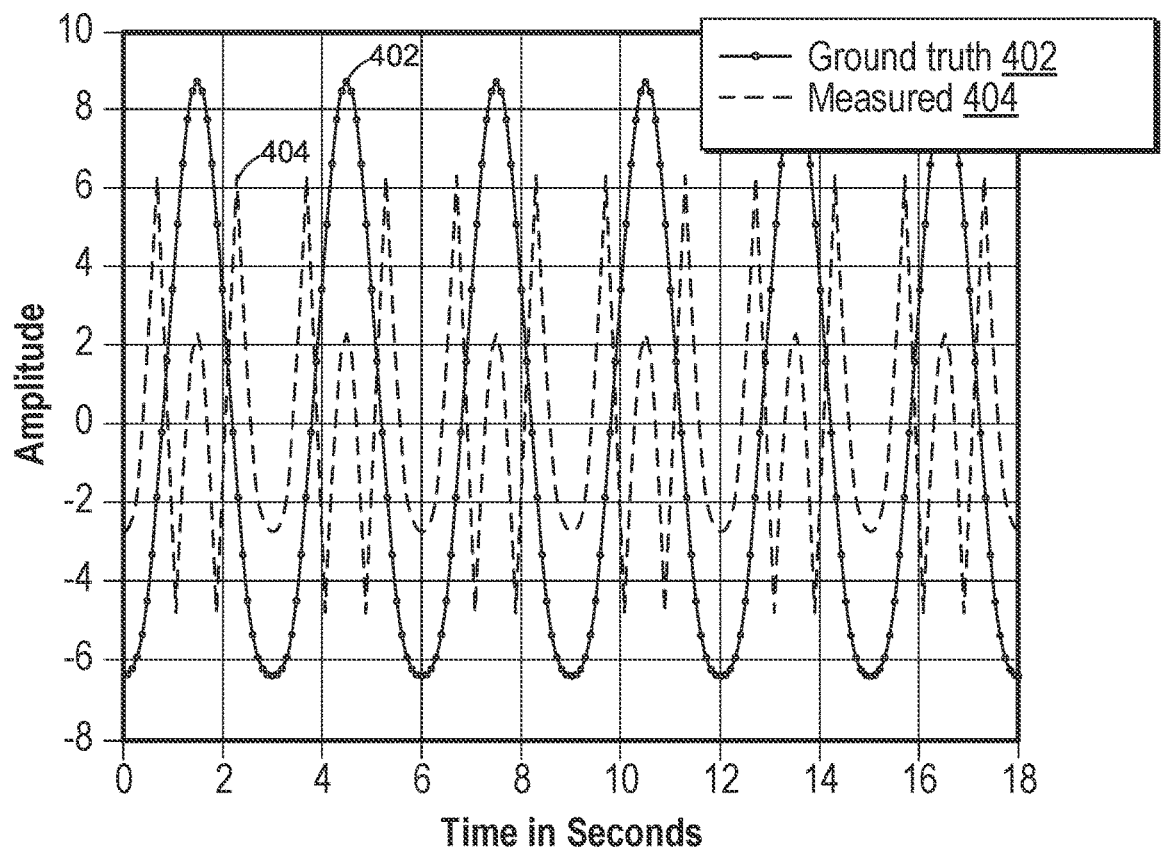
FIG. 4A illustrates example time domain breathing waveforms with phase ambiguity, in accordance with one or more example embodiments of the present disclosure.

FIG. 4A illustrates example time domain breathing waveforms 400 with phase ambiguity, in accordance with one or more example embodiments of the present disclosure.

Referring to FIG. 4A, the time domain breathing waveforms 400 include a ground truth wave 402 (e.g., accessible to the device 102 of FIG. 1) and a measured wave 404 (e.g., measured by the device 102 of FIG. 1). Because of the phase ambiguity described with respect to FIG. 3C, the measured wave 404 differs significantly from the ground truth wave 402.

Figure 4B:
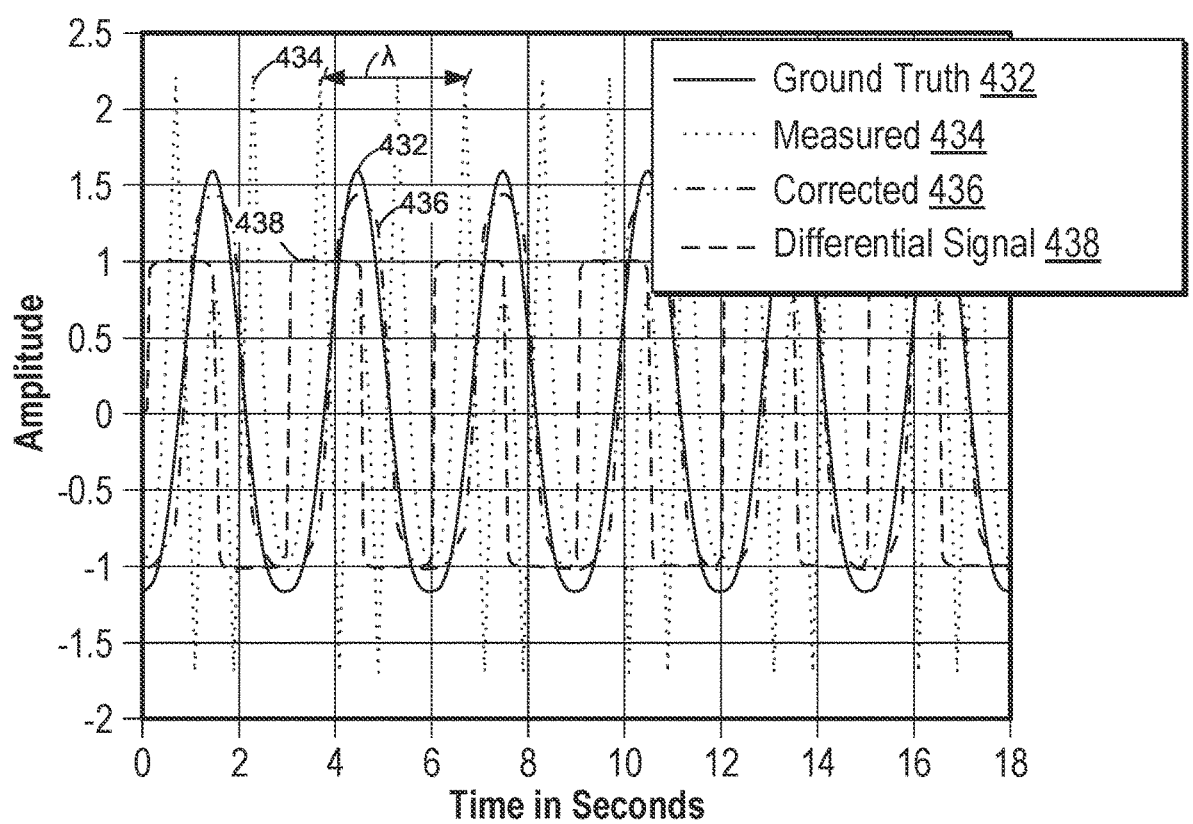
FIG. 4B illustrates example time domain breathing waveforms with phase disambiguation, in accordance with one or more example embodiments of the present disclosure.

FIG. 4B illustrates example time domain breathing waveforms 430 with phase disambiguation, in accordance with one or more example embodiments of the present disclosure.

Referring to FIG. 4B, the time domain breathing waveforms 430 include a ground truth waveform 432 (e.g., accessible to the device 102 of FIG. 1), a measured wave 434 (e.g., the wave based on the RF signal measured by the device 102 of FIG. 1), a corrected wave 436, and a differential signal 438 (e.g., a corrective signal) applied to the measured wave 434 to generate the corrected wave 436 as explained further below.

In particular, for a subcarrier (e.g., of the measured wave) with index "j," the subcarrier may be represented as Equation (1) above. Similarly, the subcarrier with index "k" may be represented as Equation (2) above.

The phase change for the $j^{th}$ subcarrier may be represented as Equation (3) above. In contrast, the differential phase change between the $j^{th}$ and $k^{th}$ subcarriers may be represented by Equation (4) defined above. In this manner, the differential phase change is smaller than the phase change, and has the benefit of being immune to phase noise because the phase noise $p_n(t)$ is absent from the differential phase equation.

In one or more embodiments, the device 102 of FIG. 1 may estimate the differential phase (e.g., for the differential signal 438) and enhance its robustness when impairments such as thermal noise and phase noise are present. One method of estimating the differential phase is to determine the phase differential of adjacent subcarriers in the RF waveform, and then average the phase differential across all the subcarriers of the RF waveform (e.g., frequency domain averaging). Another method of estimating the differential phase is to determine the phase differential of each subcarrier with the end (e.g., edge) subcarriers of the RF waveform, and to determine weighted averages (e.g., based on the frequency difference) across all the subcarriers of the RF waveform (e.g., frequency domain weighted averaging). Another method of estimating the differential phase is to correct an erroneous isolated differential phase measurement of the RF waveform (e.g., time domain state machine). Differential phase is a binary signal (e.g., plus or minus) and has the same periodicity as the RF breathing waveform. The differential phase may indicate the direction of breathing motion (e.g., inwards or outwards). When an isolated differential phase measurement is erroneous (e.g., flips in sign from plus to minus), the device 102 may correct the measurement using the preceding and subsequent measurements having the correct sign. A finite state machine may be used to correct the isolated errors.

Figure 4C:
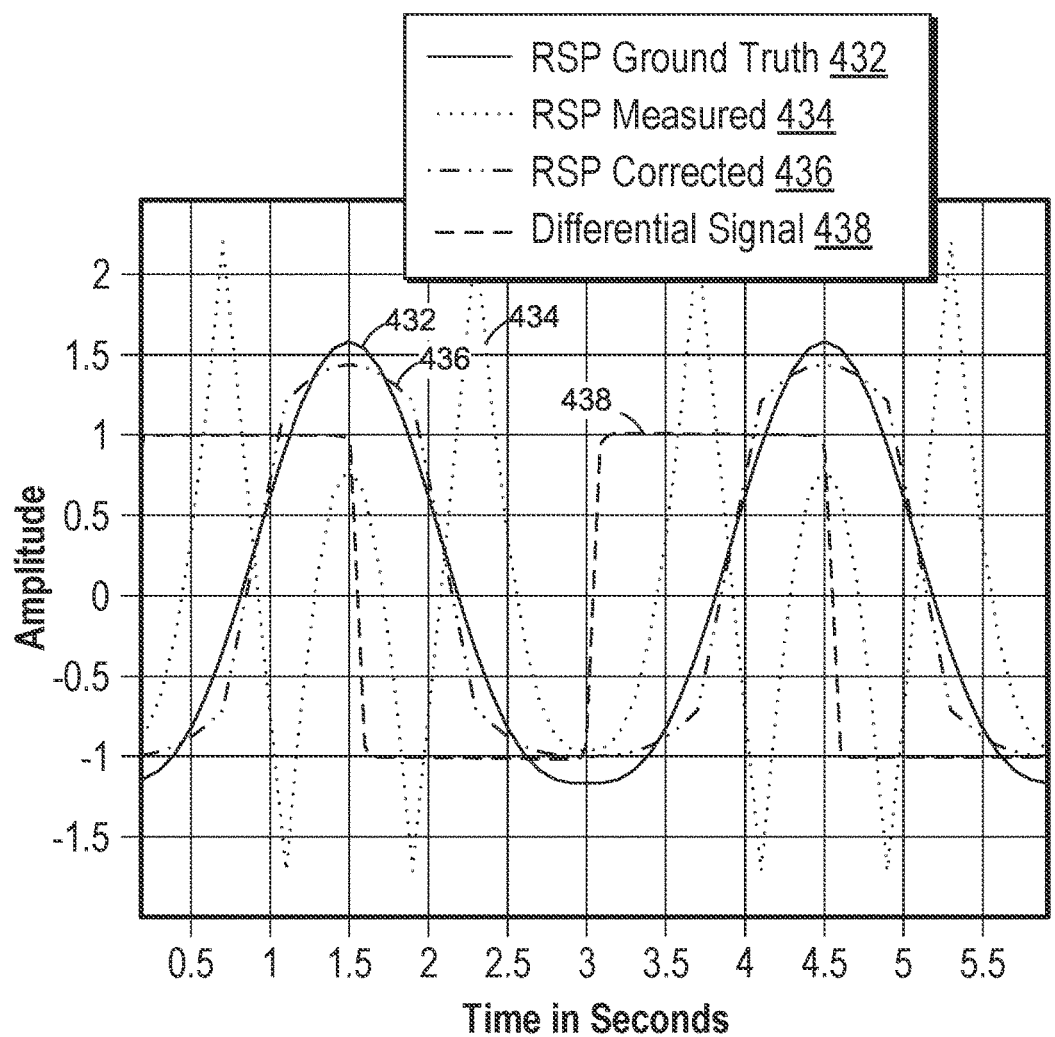
FIG. 4C illustrates example time domain breathing waveforms with phase disambiguation, in accordance with one or more example embodiments of the present disclosure.

In one or more embodiments, a device may use a correcting signal to correct a measured RF waveform indicative of breathing. The correction signal may be determined using one of the above-described methods for estimating the differential phase. By applying the correction signal to the measured RF waveform that is generated based on phase ambiguity, the device 102 may generate a corrected RF waveform that is more representative of a ground truth breathing waveform, and therefore may allow the device 102 or another device (e.g., the one or more additional devices 130 of FIG. 1) to analyze the corrected RF waveform for health and/or sleep determinations. FIG. 4C illustrates example time domain breathing waveforms 460 with phase disambiguation, in accordance with one or more example embodiments of the present disclosure.

Referring to FIG. 4C, the time domain breathing waveforms 460 include the time domain breathing waveforms 430 of FIG. 4B, but shown in a smaller time period to provide a more-detailed view of the time domain breathing waveforms 430.

Application of the differential signal 438 as a correcting signal to the measured wave 434 to generate the corrected wave 436 may occur as follows. When the differential signal 438 indicates an increasing phase trend, but the measured wave 434 indicates a decreasing phase trend (e.g., at time i=1), the correction of the measured wave 434 may include a use of phase wrapping (e.g., adding a forward $2\pi$ phase jump to the measured wave 434) to generate the corrected wave 436: Corrected wave 436($i$)=Corrected wave 436($i$-1)+$2\pi$+(measured wave 434($i$)-measured wave 434($i$-1)). When the differential signal 438 indicates a decreasing phase trend, but the measured wave 434 indicates an increasing phase trend, the correction of the measured wave 434 may include phase wrapping (e.g., adding a backward $2\pi$ phase jump to the measured wave 434) to generate the corrected wave 436: Corrected wave 436($i$)=Corrected wave 436($i$-1)-$2\pi$+(measured wave 434($i$)-measured wave 434($i$-1)). When both the differential signal 438 and the measured wave 434 indicate a positive or negative phase trend (e.g., both indicate a positive phase trend or both indicate a negative phase trend), no correction of the measured wave 434 may be required: Corrected wave 436($i$)=Corrected wave 436($i$-1)+(measured wave 434($i$)-measured wave 434($i$-1)).

In one scenario, the phase trend for the differential signal 438 may be positive (e.g., a positive value or changing from a negative value to a positive value), and the phase trend for the measured wave 434 also may be positive (e.g., increasing). Such is the scenario at time 0.5 seconds. In this scenario, no correction of the measured wave 434 may be required: Corrected wave 436($i$)=Corrected wave 436($i$-1)+(measured wave 434($i$)-measured wave 434($i$-1)). In other words, the phase correction to the measured wave 434 may be zero. In this manner, the corrected wave 436 may continue to trend positive at time 0.5 seconds.

In another scenario, the phase trend for the differential signal 438 may be negative (e.g., a negative value or changing from a positive value to a negative value), and the phase trend for the measured wave 434 also may be negative (e.g., decreasing). Such is the scenario at time 1.7 seconds. In this scenario, no correction of the measured wave 434 may be required: Corrected wave 436($i$)=Corrected wave 436($i$-1)+(measured wave 434($i$)-measured wave 434($i$-1)). In other words, the phase correction to the measured wave 434 may be zero. In this manner, the corrected wave 436 may continue to trend negative at time 1.7 seconds.

In another scenario, the phase trend for the differential signal 438 may be positive (e.g., a positive value or changing from a negative value to a positive value), and the phase trend for the measured wave 434 may be negative (e.g., decreasing). Such is the scenario at time 1.0 seconds. In this scenario, the correction of the measured wave 434 may include a use of phase wrapping (e.g., adding a forward $2\pi$ phase jump to the measured wave 434) to generate the corrected wave 436: Corrected wave 436($i$)=Corrected wave 436($i$-1)+$2\pi$+(measured wave 434($i$)-measured wave 434($i$-1)). In other words, the phase correction to the measured wave 434 may be a positive $2\pi$ value (e.g., a full cycle phase wrapping). In this manner, even though the phase trend for the measured wave 434 may be negative, the corrected wave 436 may continue to trend positive at time 1.0 seconds.

In another scenario, the phase trend for the differential signal 438 may be negative (e.g., a negative value or changing from a positive value to a negative value), and the phase trend for the measured wave 434 may be positive (e.g., increasing). Such is the scenario at time 2.0 seconds. In this scenario, the correction of the measured wave 434 may include phase wrapping (e.g., adding a backward $2\pi$ phase jump to the measured wave 434) to generate the corrected wave 436: Corrected wave 436($i$)=Corrected wave 436($i$-1)-$2\pi$±(measured wave 434($i$)-measured wave 434($i$-1)). In other words, the phase correction to the measured wave 434 may be a negative $2\pi$ value (e.g., a full cycle phase wrapping). In this manner, even though the phase trend for the measured wave 434 may be positive, the corrected wave 436 may continue to trend negative at time 2.0 seconds.

Figure 5A:
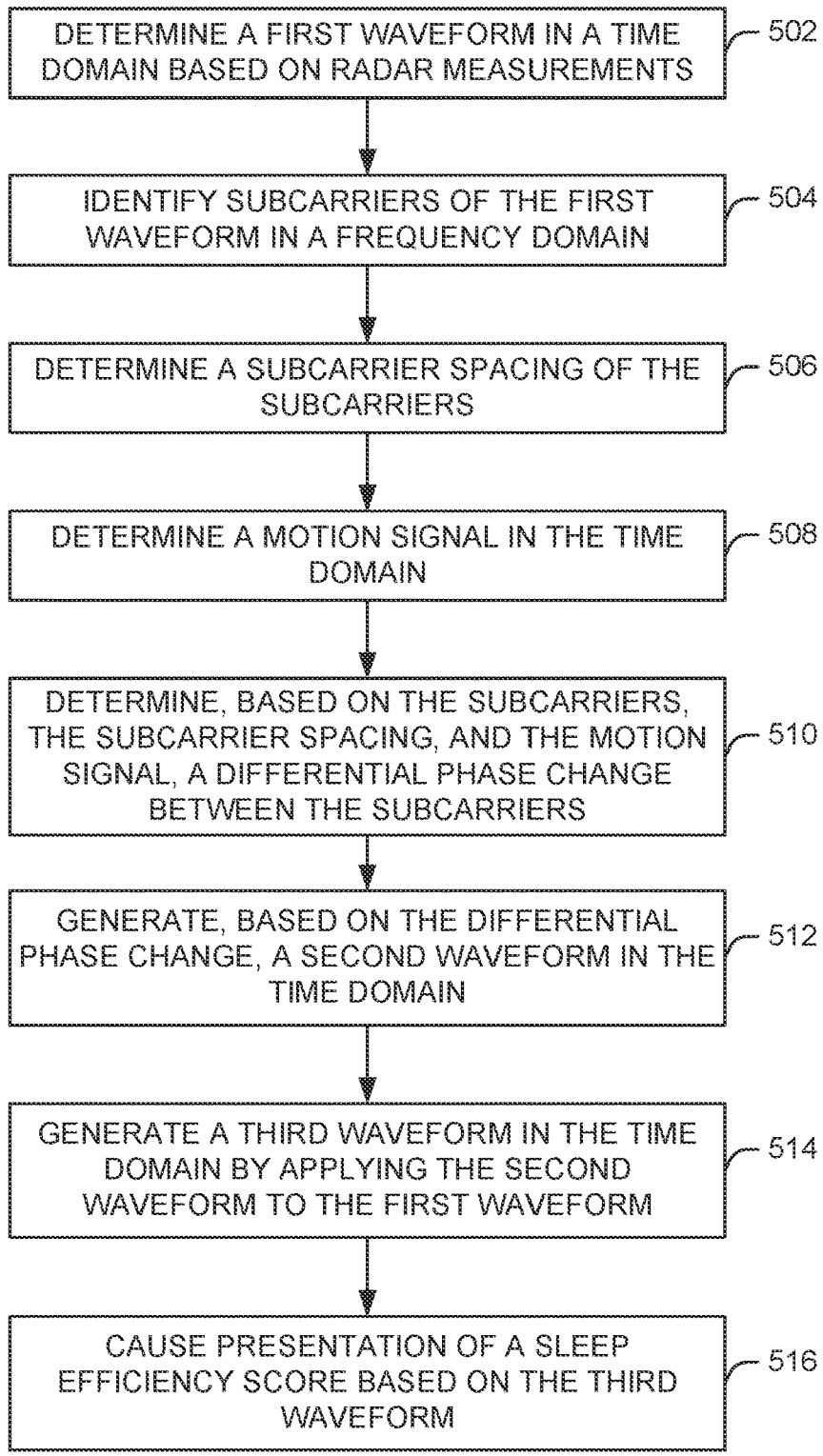
FIG. 5A illustrates a flow diagram for a process for phase disambiguation for radar-based breathing measurements, in accordance with one or more example embodiments of the present disclosure.

FIG. 5A illustrates a flow diagram for a process 500 for phase disambiguation for radar-based breathing measurements, in accordance with one or more example embodiments of the present disclosure.

At block 502, a system (or device, e.g., device 102 of FIG. 1 and/or the one or more additional devices 130 of FIG. 1) may determine a first waveform in a time domain (e.g., the measured wave 434 of FIG. 4B). The system may determine the first waveform based on detected radar-signals (e.g., the radar signals 104 of FIG. 1) detected by the system or another device (e.g., provided to the system by the other device). The first waveform may exhibit phase ambiguity (e.g., as shown in FIG. 3C) due to the low sampling rate used to detect the radar signals.

At block 504, the system may identify subcarriers (e.g., the subcarriers 202-216 of FIG. 2) of the detected radar signal used to generate the first waveform, the subcarriers being in the frequency domain. In particular, radar waveforms, such as stepped frequency continuous-waveform, may include multiple subcarriers in the frequency domain. The phase per subcarrier may undergo more than half a cycle excursion (e.g., an excursion in the first waveform from a starting point as shown in FIGS. 3A-3C) in response to motion (e.g., the person 106 of FIG. 1 breathing, vibrations of a machine, etc.), thereby resulting in the phase ambiguity shown in FIG. 3C.

At block 506, the system may determine subcarrier spacing of the subcarriers. Respective subcarriers may be spaced by a constant step value (e.g., $\Delta f$ of FIG. 2), and therefore may have indexes referring to their location on a frequency spectrum. At block 508, the system may determine a motion signal in the time domain. The motion signal d(t) may represent the physical motion that caused the first waveform (e.g., the person 106 of FIG. 1 breathing, mechanical vibrations, etc.).

At block 510, the system may determine, based on the subcarriers, the subcarrier spacing, and the motion signal, a differential phase change between the subcarriers. In particular, for a subcarrier (e.g., of the measured first waveform) with index "j," the subcarrier may be represented as Equation (1) defined above. Similarly, the subcarrier with index "k" may be represented as Equation (2) defined above.

The phase change for the $j^{th}$ subcarrier may be represented as Equation (3) as defined above. In contrast, the differential phase change between the $j^{th}$ and $k^{th}$ subcarriers may be represented by Equation (4) defined above. In this manner, the differential phase change is smaller than the phase change, and has the benefit of being immune to phase noise because the phase noise $p_n(t)$ is absent from the differential phase equation.

At block 512, the system may generate, based on the differential phase, a second waveform in the time domain. For example, the differential phase change may correspond to the differential signal 438 of FIG. 4B (e.g., the second waveform). The second waveform as the differential phase may be used as a correcting signal to apply to the first waveform to remove the phase ambiguity of the first waveform.

At block 514, the system may generate a third waveform (e.g., the corrected wave 436 of FIG. 4B) by applying the second waveform to the first waveform. By using the phase differential between subcarriers to determine the direction of motion (e.g., outwards vs. inwards in terms of breathing), phase ambiguity of the first waveform may be eliminated because the phased differential phase excursion magnitude is such a small fraction of a 360 degree cycle of the first waveform, and the system also may determine the direction of motion based on the differential phase. By determining the direction of motion and eliminating phase ambiguity, the system may generate the third waveform, which should more closely resemble a ground truth waveform (e.g., the ground truth waveform 432 of FIG. 4B). Using FIGS. 4B and 4C as examples, application of the differential signal 438 as a correcting signal to the measured wave 434 to generate the corrected wave 436 may occur as follows. When the differential signal 438 indicates an increasing phase trend, but the measured wave 434 indicates a decreasing phase trend (e.g., at time i=1), the correction of the measured wave 434 may include a use of phase wrapping (e.g., adding a forward $2\pi$ phase jump to the measured wave 434) to generate the corrected wave 436: Corrected wave 436(i)=Corrected wave 436(i−1)+2π+(measured wave 434 (i)−measured wave 434(i−1)). When the differential signal 438 indicates a decreasing phase trend, but the measured wave 434 indicates an increasing phase trend, the correction of the measured wave 434 may include phase wrapping (e.g., adding a backward $2\pi$ phase jump to the measured wave 434) to generate the corrected wave 436: Corrected wave 436(i)=Corrected wave 436(i−1)−2π+(measured wave 434(i)−measured wave 434(i−1)). When both the differential signal 438 and the measured wave 434 indicate a positive or negative phase trend (e.g., both indicate a positive phase trend or both indicate a negative phase trend), no correction of the measured wave 434 may be required: Corrected wave 436(i)=Corrected wave 436(i−1)+(measured wave 434(i)−measured wave 434(i−1)). Examples of applying the phase correction based on the positive/negative trends of the measured wave 434 and the differential signal 438 are explained above with respect to FIG. 4C.

At block 516, the system may determine and/or cause presentation of a sleep efficiency score (e.g., time asleep vs. time awake in bed as monitored by the system being proximal to a bed as shown in FIG. 1) and/or other sleep information based on the third waveform. The system may use the third waveform to determine when a person (e.g., to whom the waveform corresponds) is awake or sleeping, when the person is breathing properly or not breathing, when the person is in particular sleep stages, recommended bed times and wake times, and the like. For example, the third waveform may be compared to known waveforms associated with different sleep stages to identify when the user is sleeping or awake, etc. The presentation may occur using the system or another device (e.g., the one or more additional devices 130 of FIG. 1). The system may control applications and/or other devices, such as by setting alarms, turning off devices, and the like.

Figure 5B:
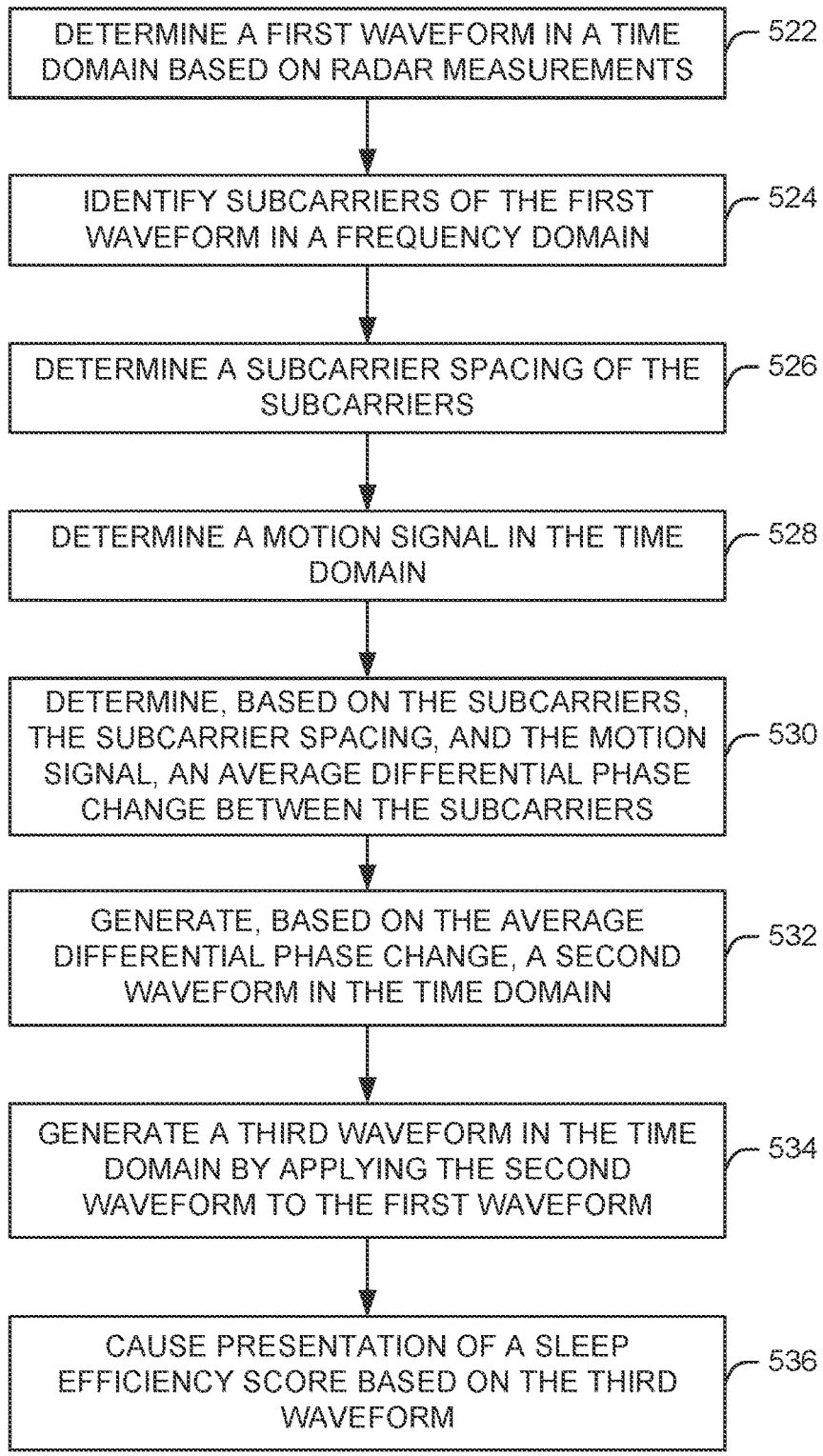
FIG. 5B illustrates a flow diagram for a process for phase disambiguation for radar-based breathing measurements, in accordance with one or more example embodiments of the present disclosure.

FIG. 5B illustrates a flow diagram for a process 520 for phase disambiguation for radar-based breathing measurements, in accordance with one or more example embodiments of the present disclosure.

At block 522, a system (or device, e.g., device 102 of FIG. 1 and/or the one or more additional devices 130 of FIG. 1) may determine a first waveform in a time domain (e.g., the measured wave 434 of FIG. 4B). The system may determine the first waveform based on detected radar-signals (e.g., the radar signals 104 of FIG. 1) detected by the system or another device (e.g., provided to the system by the other device). The first waveform may exhibit phase ambiguity (e.g., as shown in FIG. 3C) due to the low sampling rate used to detect the radar signals.

At block 524, the system may identify subcarriers (e.g., the subcarriers 202-216 of FIG. 2) of the detected radar signal used to generate the first waveform, the subcarriers being in the frequency domain. In particular, radar waveforms, such as stepped frequency continuous-waveform, may include multiple subcarriers. The phase per subcarrier may undergo more than half a cycle excursion of the first waveform in response to motion (e.g., the person 106 of FIG. 1 breathing, vibrations of a machine, etc.), thereby resulting in the phase ambiguity shown in FIG. 3C.

At block 526, the system may determine subcarrier spacing of the subcarriers. Respective subcarriers may be spaced by a constant step value (e.g., $\Delta f$ of FIG. 2), and therefore may have indexes referring to their location on a frequency spectrum. At block 528, the system may determine a motion signal in the time domain. The motion signal d(t) may represent the physical motion that caused the first waveform (e.g., the person 106 of FIG. 1 breathing, mechanical vibrations, etc.).

At block 530, the system may determine, based on the subcarriers, the subcarrier spacing, and the motion signal, an average differential phase change between the subcarriers. For example, using adjacent subcarriers (e.g., the $j^{th}$ and $k^{th}$ subcarriers described above), the system may determine the phase differential between the $j^{th}$ and $k^{th}$ subcarriers as Equation (4) defined above, or significantly less than $2\pi$ when d(t) is on the order of $$\frac{\lambda}{2}$$

because $$\frac{(j-k)\Delta f}{c} \cdot \frac{\lambda}{2} \ll \frac{1}{2}.$$

The differential phase change may be determined using non-adjacent subcarriers as well. Using the differential phase change between any two subcarriers of the first waveform, the system may average the differential phase change across all subcarriers of the first waveform.

At block 532, the system may generate, based on the average differential phase, a second waveform in the time domain. For example, the average differential phase change may correspond to the differential signal 438 of FIG. 4B (e.g., the second waveform). The second waveform as the average differential phase may be used as a correcting signal to apply to the first waveform to remove the phase ambiguity of the first waveform.

At block 534, the system may generate a third waveform (e.g., the corrected wave 436 of FIG. 4B) by applying the second waveform to the first waveform. By using the average phase differential between subcarriers to determine the direction of motion (e.g., outwards vs. inwards in terms of breathing), phase ambiguity of the first waveform may be eliminated because the phased differential phase excursion magnitude is such a small fraction of a 360 degree cycle of the first waveform, and the system also may determine the direction of motion based on the differential phase. By determining the direction of motion and eliminating phase ambiguity, the system may generate the third waveform, which should more closely resemble a ground truth waveform (e.g., the ground truth waveform 432 of FIG. 4B). Using FIGS. 4B and 4C as examples, application of the differential signal 438 as a correcting signal to the measured wave 434 to generate the corrected wave 436 may occur as follows. When the differential signal 438 indicates an increasing phase trend, but the measured wave 434 indicates a decreasing phase trend (e.g., at time i=1), the correction of the measured wave 434 may include a use of phase wrapping (e.g., adding a forward $2\pi$ phase jump to the measured wave 434) to generate the corrected wave 436: Corrected wave 436(i)=Corrected wave 436(i−1)+2π+(measured wave 434(i)−measured wave 434(i−1)). When the differential signal 438 indicates a decreasing phase trend, but the measured wave 434 indicates an increasing phase trend, the correction of the measured wave 434 may include phase wrapping (e.g., adding a backward $2\pi$ phase jump to the measured wave 434) to generate the corrected wave 436: Corrected wave 436(i)=Corrected wave 436(i−1)−2π+(measured wave 434(i)−measured wave 434(i−1)). When both the differential signal 438 and the measured wave 434 indicate a positive or negative phase trend (e.g., both indicate a positive phase trend or both indicate a negative phase trend), no correction of the measured wave 434 may be required: Corrected wave 436(i)=Corrected wave 436(i−1)+(measured wave 434(i)−measured wave 434(i−1)). Examples of applying the phase correction based on the positive/negative trends of the measured wave 434 and the differential signal 438 are explained above with respect to FIG. 4C.

At block 536, the system may determine and/or cause presentation of a sleep efficiency score (e.g., time asleep vs. time awake in bed as monitored by the system being proximal to a bed as shown in FIG. 1) and/or other sleep information based on the third waveform. The system may use the third waveform to determine when a person (e.g., to whom the waveform corresponds) is awake or sleeping, when the person is breathing properly or not breathing, when the person is in particular sleep stages, recommended bed times and wake times, and the like. For example, the third waveform may be compared to known waveforms associated with different sleep stages to identify when the user is sleeping or awake, etc. The presentation may occur using the system or another device (e.g., the one or more additional devices 130 of FIG. 1). The system may control applications and/or other devices, such as by setting alarms, turning off devices, and the like.

Figure 5C:
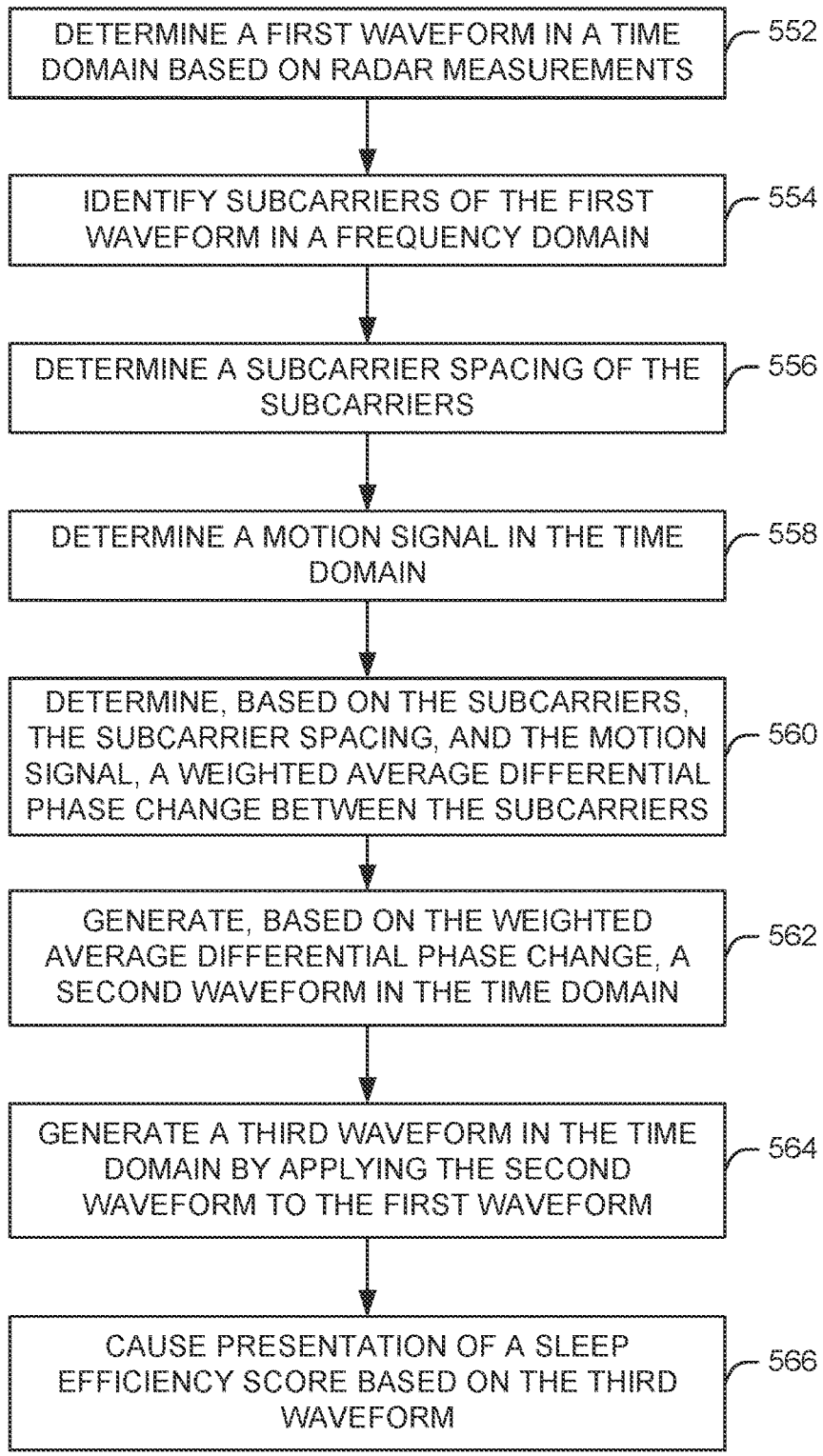
FIG. 5C illustrates a flow diagram for a process for phase disambiguation for radar-based breathing measurements, in accordance with one or more example embodiments of the present disclosure.

FIG. 5C illustrates a flow diagram for a process 550 for phase disambiguation for radar-based breathing measurements, in accordance with one or more example embodiments of the present disclosure.

At block 552, a system (or device, e.g., device 102 of FIG. 1 and/or the one or more additional devices 130 of FIG. 1) may determine a first waveform in a time domain (e.g., the measured wave 434 of FIG. 4B). The system may determine the first waveform based on radar-signals (e.g., the radar signals 104 of FIG. 1) detected by the system or another device (e.g., provided to the system by the other device). The first waveform may exhibit phase ambiguity (e.g., as shown in FIG. 3C) due to the low sampling rate used to detect the radar signals.

At block 554, the system may identify subcarriers (e.g., the subcarriers 202-216 of FIG. 2) of the radar signal used to generate the first waveform, the subcarriers being in the frequency domain. In particular, radar waveforms, such as stepped frequency continuous-waveform, may include multiple subcarriers. The phase per subcarrier may undergo more than half a cycle excursion of the first waveform in response to motion (e.g., the person 106 of FIG. 1 breathing, vibrations of a machine, etc.), thereby resulting in the phase ambiguity shown in FIG. 3C.

At block 556, the system may determine subcarrier spacing of the subcarriers. Respective subcarriers may be spaced by a constant step value (e.g., $\Delta f$ of FIG. 2), and therefore may have indexes referring to their location on a frequency spectrum. At block 558, the system may determine a motion signal in the time domain. The motion signal d(t) may represent the physical motion that caused the first waveform (e.g., the person 106 of FIG. 1 breathing, mechanical vibrations, etc.).

At block 560, the system may determine, based on the subcarriers, the subcarrier spacing, and the motion signal, a weighted average differential phase change between the subcarriers. For example, using subcarriers j and k, the differential phase change may be Equation (4) defined above, or significantly less than $2\pi$ when d(t) is about because $$\frac{(j-k)\Delta f}{c} \cdot \frac{\lambda}{2} \ll \frac{1}{2}.$$

The differential phase change may be determined between any subcarrier and the end subcarriers (e.g., subcarriers 202 and 216 of FIG. 2). Based on the frequency difference of the respective subcarriers, the system may determine a weighted average of the phase differential of all subcarriers of the first waveform.

At block 562, the system may generate, based on the weighted average differential phase, a second waveform in the time domain. For example, the weighted average differential phase change may correspond to the differential signal 438 of FIG. 4B (e.g., the second waveform). The second waveform as the weighted average differential phase may be used as a correcting signal to apply to the first waveform to remove the phase ambiguity of the first waveform.

At block 564, the system may generate a third waveform (e.g., the corrected wave 436 of FIG. 4B) by applying the second waveform to the first waveform. By using the weighted average phase differential between subcarriers to determine the direction of motion (e.g., outwards vs. inwards in terms of breathing), phase ambiguity of the first waveform may be eliminated because the phased differential phase excursion magnitude is such a small fraction of a 360 degree cycle of the first waveform, and the system also may determine the direction of motion based on the differential phase. By determining the direction of motion and eliminating phase ambiguity, the system may generate the third waveform, which should more closely resemble a ground truth waveform (e.g., the ground truth waveform 432 of FIG. 4B). Using FIGS. 4B and 4C as examples, application of the differential signal 438 as a correcting signal to the measured wave 434 to generate the corrected wave 436 may occur as follows. When the differential signal 438 indicates an increasing phase trend, but the measured wave 434 indicates a decreasing phase trend (e.g., at time i=1), the correction of the measured wave 434 may include a use of phase wrapping (e.g., adding a forward 2π phase jump to the measured wave 434) to generate the corrected wave 436: Corrected wave 436(*i*)=Corrected wave 436(*i*−1)+2π+(measured wave 434(*i*)−measured wave 434(*i*−1)). When the differential signal 438 indicates a decreasing phase trend, but the measured wave 434 indicates an increasing phase trend, the correction of the measured wave 434 may include phase wrapping (e.g., adding a backward 2π phase jump to the measured wave 434) to generate the corrected wave 436: Corrected wave 436(*i*)=Corrected wave 436(*i*−1)−2π+(measured wave 434(*i*)−measured wave 434(*i*−1)). When both the differential signal 438 and the measured wave 434 indicate a positive or negative phase trend (e.g., both indicate a positive phase trend or both indicate a negative phase trend), no correction of the measured wave 434 may be required: Corrected wave 436(*i*)=Corrected wave 436(*i*−1)+(measured wave 434(*i*)−measured wave 434(*i*−1)). Examples of applying the phase correction based on the positive/negative trends of the measured wave 434 and the differential signal 438 are explained above with respect to FIG. 4C.

At block 566, the system may determine and/or cause presentation of a sleep efficiency score (e.g., time asleep vs. time awake in bed as monitored by the system being proximal to a bed as shown in FIG. 1) and/or other sleep information based on the third waveform. The system may use the third waveform to determine when a person (e.g., to whom the waveform corresponds) is awake or sleeping, when the person is breathing properly or not breathing, when the person is in particular sleep stages, recommended bed times and wake times, and the like. For example, the third waveform may be compared to known waveforms associated with different sleep stages to identify when the user is sleeping or awake, etc. The presentation may occur using the system or another device (e.g., the one or more additional devices 130 of FIG. 1). The system may control applications and/or other devices, such as by setting alarms, turning off devices, and the like.

Figure 5D:
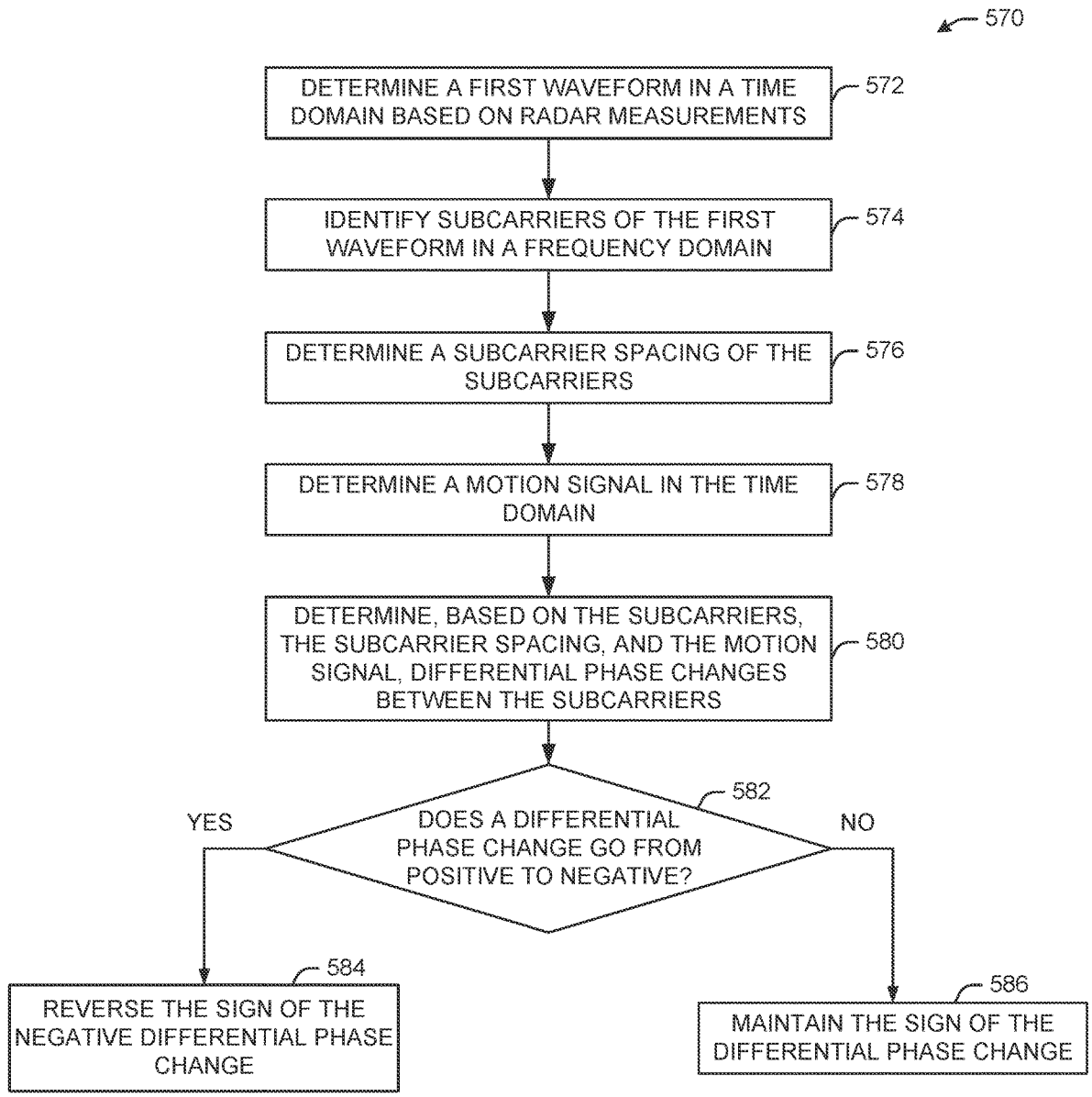
FIG. 5D illustrates a flow diagram for a process for phase disambiguation for radar-based breathing measurements, in accordance with one or more example embodiments of the present disclosure.

FIG. 5D illustrates a flow diagram for a process 570 for phase disambiguation for radar-based breathing measurements, in accordance with one or more example embodiments of the present disclosure.

At block 572, a system (or device, e.g., device 102 of FIG. 1 and/or the one or more additional devices 130 of FIG. 1) may determine a first waveform in a time domain (e.g., the measured wave 434 of FIG. 4B). The system may determine the first waveform based on radar-signals (e.g., the radar signals 104 of FIG. 1) detected by the system or another device (e.g., provided to the system by the other device). The first waveform may exhibit phase ambiguity (e.g., as shown in FIG. 3C) due to the low sampling rate used to detect the radar signals.

At block 574, the system may identify subcarriers (e.g., the subcarriers 202-216 of FIG. 2) of the radar signal used to generate the first waveform, the subcarriers being in the frequency domain. In particular, radar waveforms, such as stepped frequency continuous-waveform, may include multiple subcarriers. The phase per subcarrier may undergo more than half a cycle excursion of the first waveform in response to motion (e.g., the person 106 of FIG. 1 breathing, vibrations of a machine, etc.), thereby resulting in the phase ambiguity shown in FIG. 3C.

At block 576, the system may determine subcarrier spacing of the subcarriers. Respective subcarriers may be spaced by a constant step value (e.g., Δf of FIG. 2), and therefore may have indexes referring to their location on a frequency spectrum. At block 578, the system may determine a motion signal in the time domain. The motion signal d(t) may represent the physical motion that caused the first waveform (e.g., the person 106 of FIG. 1 breathing, mechanical vibrations, etc.).

At block 580, the system may determine, based on the subcarriers, the subcarrier spacing, and the motion signal, differential phase changes between respective subcarriers. For example, using subcarriers j and k, the differential phase change may be Equation (4) defined above, or significantly less than 2π when d(t) is about $$\frac{\lambda}{2}$$

because $$\frac{(j-k)\Delta f}{c} \cdot \frac{\lambda}{2} \ll \frac{1}{2}.$$

The differential phase may be a binary signal with positive and negative values and having the same periodicity as a breathing waveform (e.g., see FIGS. 4B and 4C), and may indicate the direction of motion.

At block 582, the system may determine when a differential phase change goes from a positive to a negative value. For example, when a differential phase change from a first subcarrier to a second subcarrier is positive, and the differential phase change from the second subcarrier to a third subcarrier is negative, the differential phase change may be said to go from a positive to a negative value (e.g., the differential signal 438 of FIGS. 4B and 4C goes from a positive to a negative value). When an isolated differential phase measurement is erroneous (e.g., flips in sign from a positive value to a negative value), the differential phase measurement may be correcting using preceding and subsequent measurements having the correct sign. For example, a finite state machine of the system may, at block 584, reverse the sign of the negative differential phase change (e.g., from a negative value to a positive value) in the time domain when the differential phase value of the subcarriers for the first waveform changes from a positive to a negative value (and may refrain from reversing/maintain, at block 586, the sign of the differential phase value when the differential phase value changes from a negative to a positive value). The differential signal 438 may be generated in this manner, and applied to the first waveform to generate the corrected waveform as explained above. Examples of applying the phase correction based on the positive/negative trends of the measured wave 434 and the differential signal 438 are explained above with respect to FIG. 4C.

Figure 6:
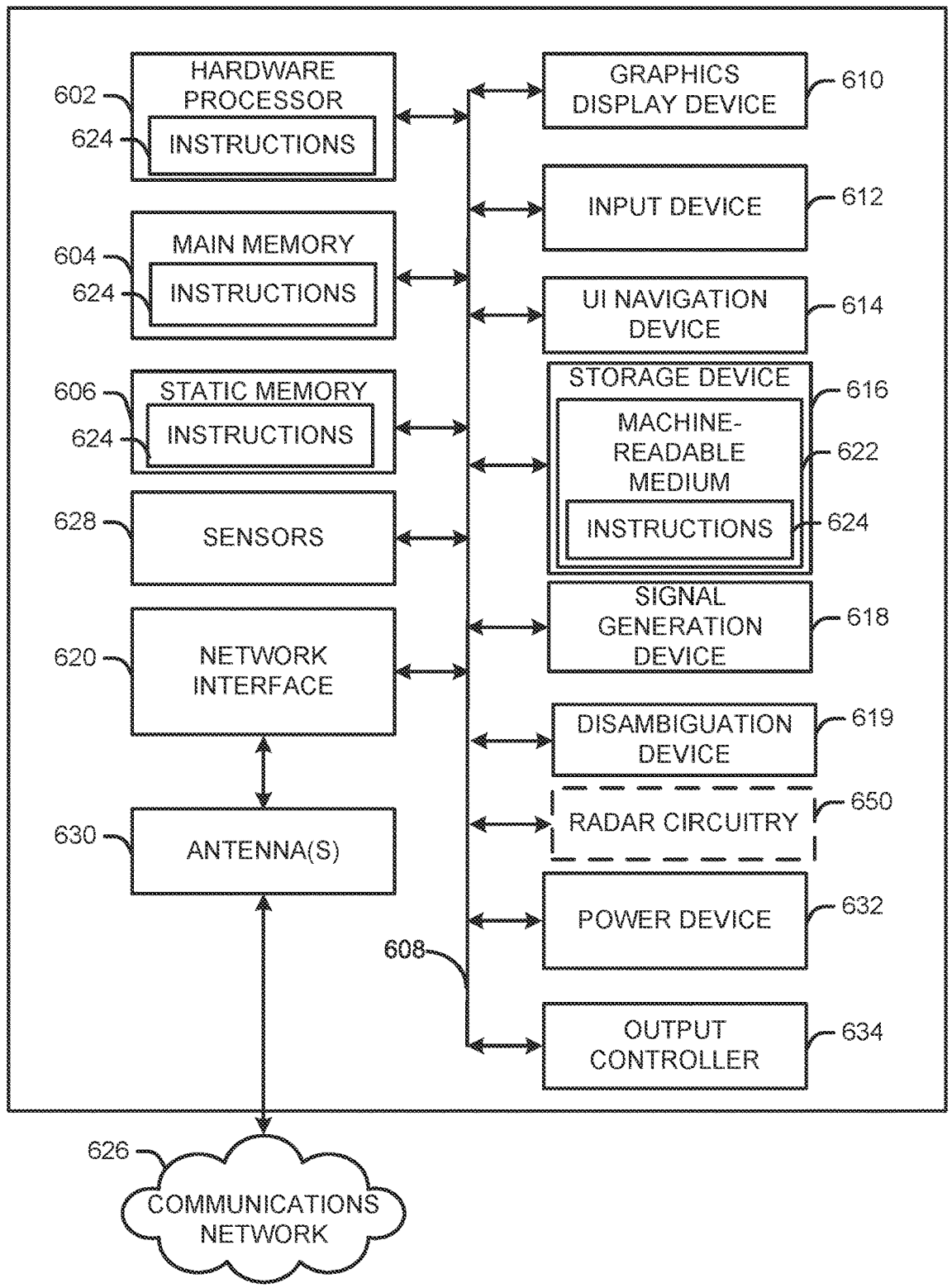
FIG. 6 illustrates a block diagram of an example machine upon which any of one or more techniques (e.g., methods) may be performed, in accordance with one or more example embodiments of the present disclosure.

FIG. 6 illustrates a block diagram of an example of a machine 600 or system (e.g., the device 102 of FIG. 1, the one or more additional devices 130 of FIG. 1) or system upon which any one or more of the techniques (e.g., methodologies) discussed herein may be performed. In other embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in Wi-Fi direct, peer-to-peer (P2P), cellular, (or other distributed) network environments. The machine 600 may be a server, a personal computer (PC), a smart home device, a tablet PC, a personal digital assistant (PDA), a mobile telephone, a wearable computer device, a web appliance, or any machine capable of executing instructions (sequential or otherwise) that specify actions to be taken by that machine, such as a base station. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions where the instructions configure the execution units to carry out a specific operation when in operation. The configuring may occur under the direction of the executions units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

The machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a power management device 632, a graphics display device 610, an alphanumeric input device 612 (e.g., a keyboard), and a user interface (UI) navigation device 614 (e.g., a mouse). In an example, the graphics display device 610, alphanumeric input device 612, and UI navigation device 614 may be a touch screen display. The machine 600 may additionally include a storage device (i.e., drive unit) 616, a signal generation device 618, a disambiguation device 619 (e.g., one or more modules capable of performing the process 500 of FIG. 5A, the process 520 of FIG. 5B, the process 550 of FIG. 5C, and/or the process 570 of FIG. 5D), a network interface device/transceiver 620 coupled to antenna(s) 630, one or more sensors 628, such as a global positioning system (GPS) sensor, or other sensor, and radar circuitry 650. The machine 600 may include an output controller 634, such as a serial (e.g., universal serial bus (USB), parallel, or other wired or wireless (e.g., infrared (IR), near field communication (NFC), etc.) connection to communicate with or control one or more peripheral devices (e.g., a printer, a card reader, etc.)).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within the static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine-readable medium" may include a single medium or multiple media (e.g., a centralized or distributed database, and/or associated caches and servers) configured to store the one or more instructions 624.

Various embodiments may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "machine-readable medium" may include any medium that is capable of storing, encoding, or carrying instructions for execution by the machine 600 and that cause the machine 600 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., electrically programmable read-only memory (EPROM), or electrically erasable programmable read-only memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device/transceiver 620 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), plain old telephone (POTS) networks, wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, and peer-to-peer (P2P) networks, among others. In an example, the network interface device/transceiver 620 may include one or more physical jacks (e.g., Ethernet, coaxial, or phone jacks) or one or more antennas to connect to the communications network 626. In an example, the network interface device/transceiver 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 600 and includes digital or analog communications signals or other intangible media to facilitate communication of such software.

The radar circuitry 650 may include radar antennae for emitting and receiving radar waves (e.g., the radar signals 104 of FIG. 1). For example, when the machine 600 is implemented as the device 102 of FIG. 1, the machine 600 may include the radar circuitry 650. The radar circuitry 650 may be capable of emitting and receiving radar waves in multiple directions at sampling the radar waves using a variety of sampling rates (e.g., using 60 GHz carrier frequency and 100 MHz subcarrier spacing, among other examples). The disambiguation device 619 may be used to disambiguate radar waveforms detected by the radar circuitry 650 (e.g., when detected and disambiguated by the same machine). In this manner, the disambiguation device 619 may include one or more modules and/or finite state machines for performing the processes described at least in FIGS. 5A-5D. The disambiguation device 619 may be included in the device 102 of FIG. 1 and/or in the one or more additional devices 130 of FIG. 1 (e.g., when the machine 600 is implemented in the one or more additional devices 130).

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

The word "exemplary" is used herein to mean "serving as an example, instance, or illustration." Any embodiment described herein as "exemplary" is not necessarily to be construed as preferred or advantageous over other embodiments. The terms "computing device," "user device," "communication station," "station," "handheld device," "mobile device," "wireless device" and "user equipment" (UE) as used herein refers to a wireless communication device such as a cellular telephone, a smartphone, a tablet, a netbook, a wireless terminal, a laptop computer, a femtocell, a high data rate (HDR) subscriber station, an access point, a printer, a point of sale device, an access terminal, or other personal communication system (PCS) device. The device may be either mobile or stationary.

As used within this document, the term "communicate" is intended to include transmitting, or receiving, or both transmitting and receiving. This may be particularly useful in claims when describing the organization of data that is being transmitted by one device and received by another, but only the functionality of one of those devices is required to infringe the claim. Similarly, the bidirectional exchange of data between two devices (both devices transmit and receive during the exchange) may be described as "communicating," when only the functionality of one of those devices is being claimed. The term "communicating" as used herein with respect to a wireless communication signal includes transmitting the wireless communication signal and/or receiving the wireless communication signal. For example, a wireless communication unit, which is capable of communicating a wireless communication signal, may include a wireless transmitter to transmit the wireless communication signal to at least one other wireless communication unit, and/or a wireless communication receiver to receive the wireless communication signal from at least one other wireless communication unit.

As used herein, unless otherwise specified, the use of the ordinal adjectives "first," "second," "third," etc., to describe a common object, merely indicates that different instances of like objects are being referred to and are not intended to imply that the objects so described must be in a given sequence, either temporally, spatially, in ranking, or in any other manner.

Some embodiments may be used in conjunction with various devices and systems, for example, a personal computer (PC), a desktop computer, a mobile computer, a laptop computer, a notebook computer, a tablet computer, a server computer, a handheld computer, a handheld device, a personal digital assistant (PDA) device, a handheld PDA device, an on-board device, an off-board device, a hybrid device, a vehicular device, a non-vehicular device, a mobile or portable device, a consumer device, a non-mobile or non-portable device, a wireless communication station, a wireless communication device, a wireless access point (AP), a wired or wireless router, a wired or wireless modem, a video device, an audio device, an audio-video (A/V) device, a wired or wireless network, a wireless area network, a wireless video area network (WVAN), a local area network (LAN), a wireless LAN (WLAN), a personal area network (PAN), a wireless PAN (WPAN), and the like.

Some embodiments may be used in conjunction with one way and/or two-way radio communication systems, cellular radio-telephone communication systems, a mobile phone, a cellular telephone, a wireless telephone, a personal communication system (PCS) device, a PDA device which incorporates a wireless communication device, a mobile or portable global positioning system (GPS) device, a device which incorporates a GPS receiver or transceiver or chip, a device which incorporates an RFID element or chip, a multiple input multiple output (MIMO) transceiver or device, a single input multiple output (SIMO) transceiver or device, a multiple input single output (MISO) transceiver or device, a device having one or more internal antennas and/or external antennas, digital video broadcast (DVB) devices or systems, multi-standard radio devices or systems, a wired or wireless handheld device, e.g., a smartphone, a wireless application protocol (WAP) device, or the like.

Some embodiments may be used in conjunction with one or more types of wireless communication signals and/or systems following one or more wireless communication protocols, for example, radio frequency (RF), infrared (IR), frequency-division multiplexing (FDM), orthogonal FDM (OFDM), time-division multiplexing (TDM), time-division multiple access (TDMA), extended TDMA (E-TDMA), general packet radio service (GPRS), extended GPRS, code-division multiple access (CDMA), wideband CDMA (WCDMA), CDMA 2000, single-carrier CDMA, multi-carrier CDMA, multi-carrier modulation (MDM), discrete multi-tone (DMT), Bluetooth®, global positioning system (GPS), Wi-Fi, Wi-Max, ZigBee, ultra-wideband (UWB), global system for mobile communications (GSM), 2G, 2.5G, 3G, 3.5G, 4G, fifth generation (5G) mobile networks, 3GPP, long term evolution (LTE), LTE advanced, enhanced data rates for GSM Evolution (EDGE), or the like. Other embodiments may be used in various other devices, systems, and/or networks.

It is understood that the above descriptions are for purposes of illustration and are not meant to be limiting.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in any applicable flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in any flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A method for determining a sleep efficiency score, the method comprising:
   determining, by a device, a first waveform from a radar signal, the radar signal comprising a plurality of subcarriers in a frequency domain;
   identifying, by the device, a first subcarrier of the plurality of subcarriers;
   identifying, by the device, a second subcarrier of the plurality of subcarriers;
   determining, by the device, a subcarrier spacing of the first and the second subcarriers;
   determining, by the device, a first signal associated with a person breathing, a first wavelength of the first signal being less than a second wavelength of the radar signal, wherein the first signal is a ground truth signal of the person breathing;
   determining, by the device, based on the first subcarrier, the second subcarrier, the subcarrier spacing, and the first signal, a first phase change differential value between the first subcarrier and the second subcarrier;
   generating, by the device, based on the first phase change differential value and the first waveform, a second waveform;
   determining, by the device, a first trend of the first waveform between a first time and a second time;
   determining, by the device, a second trend of the second waveform between the first time and the second time;
   applying, by the device, a phase correction to the first waveform based on the first trend and the second trend;
   generating, by the device, a third waveform based on applying the phase correction to the first waveform; and
   determining, by the device and based on the third waveform, a sleep efficiency score associated with the person.

2. The method of claim 1, wherein the first subcarrier and the second subcarrier are adjacent to one another, and wherein generating the second waveform further comprises:
   identifying a third subcarrier of the plurality of subcarriers;
   determining, based on the subcarrier spacing and the first signal, a second phase change differential value between the second subcarrier and the third subcarrier; and
   determining, based on the first phase change differential value and the second phase change differential value, an average phase change differential value of the plurality of subcarriers.

3. The method of claim 1, wherein the first subcarrier is an edge subcarrier of the plurality of subcarriers, and wherein generating the second waveform further comprises:
   identifying a third subcarrier of the plurality of subcarriers;
   determining a second phase change differential value between the first subcarrier and the third subcarrier; and
   determining a weighted average phase change differential value for the plurality of subcarriers based on the first phase change differential value, the second phase change differential value, and the subcarrier spacing.

4. The method of claim 1, and wherein generating the second waveform further comprises:
   identifying a third subcarrier of the plurality of subcarriers;
   determining a second phase change differential value between the second subcarrier and the third subcarrier, wherein the second waveform is further based on the second phase change differential value;
   determining that the first phase change differential value is greater than zero;
   determining that the second phase change differential value is less than zero; and
   changing the second phase change differential value to a value greater than zero.

5. A method for disambiguating phase in radar-based waveforms, the method comprising:
   determining, by a device, a first waveform from a radar signal, the radar signal including a first subcarrier and a second subcarrier in a frequency domain;
   determining, by the device and using the radar signal, a first signal associated with motion of an object, wherein the first signal is a ground truth signal associated with the motion;
   determining, by the device, based on the first subcarrier, the second subcarrier, a subcarrier spacing of the first subcarrier and the second subcarrier, and the first signal, a first phase change differential value between the first subcarrier and the second subcarrier;
   generating, by the device, based on the first phase change differential value and the first waveform, a second waveform;
   determining, by the device, based on the first waveform and the second waveform, a phase correction value;
   generating, by the device, a third waveform by applying the phase correction value to the first waveform; and determining, by the device, based on the third waveform, a value associated with the motion of the object.

6. The method of claim 5, wherein determining the phase correction value comprises:
determining a first trend of the first waveform between a first time and a second time;
determining a second trend of the second waveform between the first time and the second time;
determining that both the first trend and the second trend are positive trends or that both the first trend and the second trend are negative trends; and
determining that the phase correction is zero.

7. The method of claim 5, wherein determining the phase correction value comprises:
determining a first trend of the first waveform between a first time and a second time;
determining a second trend of the second waveform between the first time and the second time;
determining that the first trend is positive;
determining that the second trend is negative; and
determining that the phase correction is a positive $2\pi$.

8. The method of claim 5, wherein determining the phase correction value comprises:
determining a first trend of the first waveform between a first time and a second time;
determining a second trend of the second waveform between the first time and the second time;
determining that the first trend is negative;
determining that the second trend is positive; and
determining that the phase correction is a negative $2\pi$.

9. The method of claim 5, wherein the first signal further comprises a third subcarrier, and wherein generating the second waveform further comprises:
determining a second phase change differential value between the second subcarrier and the third subcarrier; and
determining, for the first signal, an average phase change differential value of the first phase change differential value and the second phase change differential value.

10. The method of claim 5, wherein the first signal comprises a third subcarrier, and wherein generating the second waveform further comprises:
determining a second phase change differential value between the first subcarrier and the third subcarrier; and
determining, for the first signal, a weighted average phase change differential value for the first subcarrier, the second subcarrier, and the third subcarrier based on the first phase change differential value, the second phase change differential value, and the subcarrier spacing.

11. The method of claim 10, wherein the first subcarrier is an edge subcarrier from among the first subcarrier, the second subcarrier, and the third subcarrier.

12. The method of claim 5, wherein the first signal comprises a third subcarrier, and wherein generating the third waveform comprises:
determining a second phase change differential value between the second subcarrier and the third subcarrier, wherein the second waveform is further based on the second phase change differential value;
determining that the first phase change differential value is greater than zero;
determining that the second phase change differential value is less than zero; and
changing the second phase change differential value to a value greater than zero.

13. The method of claim 5, wherein:
the object is a human being;
the radar signal is associated with breathing activity of the human being;
the first signal is associated with motion of a portion of the human being during the breathing activity; and
the value is a sleep efficiency score associated with the human being.

14. A device comprising:
a radar device configured to emit and detect radar signals; and
memory coupled to at least one processor, the at least one processor configured to:
determine, based on the radar signals, a first waveform, the radar signals comprising a first subcarrier and a second subcarrier in a frequency domain;
determine a first signal associated with motion of an object, wherein the first signal is a ground truth signal associated with the motion;
determine, based on the first subcarrier, the second subcarrier, a subcarrier spacing of the first subcarrier and the second subcarrier, and the first signal, a first phase change differential value between the first subcarrier and the second subcarrier;
generate, based on the first phase change differential value and the first waveform, a second waveform;
determine, based on the first waveform and the second waveform, a phase correction value;
generate, based on the first waveform, a third waveform by applying the phase correction value to the first waveform; and
determine, based on the third waveform, a value associated with the motion of the object.

15. The device of claim 14, wherein to determine the phase correction value comprises the at least one processor being further configured to:
determine a first trend of the first waveform between a first time and a second time;
determine a second trend of the second waveform between the first time and the second time;
determine that both the first trend and the second trend are positive trends or that both the first trend and the second trend are negative trends; and
determine that the phase correction is zero.

16. The device of claim 14, wherein to determine the phase correction value comprises the at least one processor being further configured to:
determine a first trend of the first waveform between a first time and a second time;
determine a second trend of the second waveform between the first time and the second time;
determine that the first trend is positive;
determine that the second trend is negative; and
determine that the phase correction is a positive $2\pi$.

17. The device of claim 14, wherein to determine the phase correction value comprises the at least one processor being further configured to:
determine a first trend of the first waveform between a first time and a second time;
determine a second trend of the second waveform between the first time and the second time;
determine that the first trend is negative;
determine that the second trend is positive; and
determine that the phase correction is a negative $2\pi$.

18. The device of claim 14, wherein the first signal further comprises a third subcarrier, and wherein to generate the second waveform comprises the at least one processor being further configured to:

determine a second phase change differential value between the second subcarrier and the third subcarrier; and determine, for the first signal, an average phase change differential value of the first phase change differential value and the second phase change differential value.

19. The device of claim 14, wherein the first signal comprises a third subcarrier, and wherein to generate the second waveform comprises the at least one processor being further configured to:
   determine a second phase change differential value between the first subcarrier and the third subcarrier; and
   determine, for the first signal, a weighted average phase change differential value for the first subcarrier, the second subcarrier, and the third subcarrier based on the first phase change differential value, the second phase change differential value, and the subcarrier spacing.

20. The device of claim 19, wherein the first subcarrier is an edge subcarrier among the first subcarrier, the second subcarrier, and the third subcarrier.

* * * * *